US011215621B2

(12) United States Patent
Yu et al.

(10) Patent No.: US 11,215,621 B2
(45) Date of Patent: Jan. 4, 2022

(54) LARGE-SCALE MAPPING OF PROTEIN-PROTEIN INTERACTIONS FROM CROSSLINKING MASS SPECTROMETRY

(71) Applicant: Cornell University, Ithaca, NY (US)

(72) Inventors: Haiyuan Yu, Ithaca, NY (US); Sheng Zhang, Ithaca, NY (US); Yugandhar Kumar, Ithaca, NY (US); Ievgen Motorykin, Carlsbad, CA (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 17/047,141

(22) PCT Filed: Apr. 12, 2019

(86) PCT No.: PCT/US2019/027296
§ 371 (c)(1),
(2) Date: Oct. 13, 2020

(87) PCT Pub. No.: WO2019/200300
PCT Pub. Date: Oct. 17, 2019

(65) Prior Publication Data
US 2021/0088531 A1    Mar. 25, 2021

Related U.S. Application Data

(60) Provisional application No. 62/657,257, filed on Apr. 13, 2018, provisional application No. 62/746,671, filed on Oct. 17, 2018.

(51) Int. Cl.
*G01N 33/48*    (2006.01)
*G01N 33/50*    (2006.01)
(Continued)

(52) U.S. Cl.
CPC ......... *G01N 33/6848* (2013.01); *G01N 30/86* (2013.01); *G01N 33/6845* (2013.01);
(Continued)

(58) Field of Classification Search
CPC ............... G01N 33/6848; G01N 30/86; G01N 33/6845; G01N 2030/8831; G06N 3/02;
(Continued)

(56) References Cited

U.S. PATENT DOCUMENTS 9,612,246 B2    4/2017 Bruce et al.
2006/0036425 A1*  2/2006 Le Cocq ............... G06T 11/206
                                                 703/22
(Continued)

FOREIGN PATENT DOCUMENTS

CA    2523976 A1    11/2004
GB    2403342 A     12/2004
(Continued)

OTHER PUBLICATIONS

H. Yu et al., "High Quality Binary Protein Interaction Map of the Yeast Interactome Network," Science, vol. 322, Oct. 3, 2008, pp. 104-110.
(Continued)

*Primary Examiner* — Russell S Negin
(74) *Attorney, Agent, or Firm* — Ryan, Mason & Lewis, LLP

(57) ABSTRACT

A processing platform in one embodiment comprises one or more processing devices each including at least one processor coupled to a memory. The processing platform is configured to implement a crosslink identification and validation algorithm for processing multiple levels of mass spectrometry data in order to identify and validate protein-protein interactions within the mass spectrometry data. In conjunction with execution of the crosslink identification and validation algorithm, the processing platform is further configured to obtain mass spectrometry spectra for each of the multiple levels, to apply a header matching filter to identify at least one potential crosslink relating one or more (Continued)

first level spectra and one or more second level spectra utilizing a plurality of third level spectra, and to apply one or more mass validation filters to identify whether or not the potential crosslink is a valid crosslink.

30 Claims, 28 Drawing Sheets

(51) Int. Cl.
  G01N 33/68 (2006.01)
  G16B 15/00 (2019.01)
  G16B 40/10 (2019.01)
  G01N 30/86 (2006.01)
  G06K 9/62 (2006.01)
  G06N 3/02 (2006.01)
  G01N 30/88 (2006.01)

(52) U.S. Cl.
  CPC ......... *G06K 9/6256* (2013.01); *G06K 9/6262* (2013.01); *G06N 3/02* (2013.01); *G16B 15/00* (2019.02); *G16B 40/10* (2019.02); *G01N 2030/8831* (2013.01)

(58) Field of Classification Search
  CPC .... G06K 9/6262; G06K 9/6256; G16B 40/10; G16B 15/00
  See application file for complete search history.

(56) References Cited

U.S. PATENT DOCUMENTS

| | | | |
|---|---|---|---|
| 2008/0090298 A1 | 4/2008 | Apffel | |
| 2011/0070596 A1 | 3/2011 | Wood et al. | |
| 2012/0145890 A1* | 6/2012 | Goodlett | H01J 49/0454 250/282 |
| 2013/0334414 A1* | 12/2013 | McAlister | H01J 49/0031 250/283 |
| 2017/0329842 A1* | 11/2017 | Ng Tari | G06F 3/04842 |
| 2019/0018019 A1 | 1/2019 | Shan et al. | |
| 2019/0034586 A1 | 1/2019 | Pirrotte et al. | |
| 2019/0043703 A1 | 2/2019 | Bern et al. | |
| 2019/0084929 A1 | 3/2019 | Luo et al. | |

FOREIGN PATENT DOCUMENTS

| | | |
|---|---|---|
| WO | 2015189255 A1 | 12/2015 |
| WO | 2017214049 A1 | 12/2017 |
| WO | PCT/US2019/027296 | 7/2019 |

OTHER PUBLICATIONS

X. Wang et al., "Three-Dimensional Reconstruction of Protein Networks Provides Insight into Human Genetic Disease," Nature Biotechnology, vol. 30, No. 2, Jan. 15, 2012, 14 pages.

J. Rappsilber, "The Beginning of a Beautiful Friendship: Cross-Linking/Mass Spectrometry and Modelling of Proteins and Multi-Protein Complexes," Journal of Structural Biology, vol. 173, No. 3, Mar. 2011, pp. 530-540.

A. Kao et al., "Development of a Novel Cross-linking Strategy for Fast and Accurate Identification of Cross-linked Peptides of Protein Complexes," Molecular & Cellular Proteomics, vol. 10, No. 1, Aug. 24, 2010, 17 pages.

A. Kao et al., "Mapping the Structural Topology of the Yeast 19S Proteasomal Regulatory Particle Using Chemical Cross-linking and Probabilistic Modeling," Molecular & Cellular Proteomics, Apr. 30, 2012, 40 pages.

F. Liu et al., "Optimized Fragmentation Schemes and Data Analysis Strategies for Proteome-Wide Cross-Link Identification," Nature Communications, May 19, 2017, 8 pages.

J. E. Elias et al., "Intensity-Based Protein Identification by Machine Learning from a Library of Tandem Mass Spectra," Nature Biotechnology, vol. 22, No. 2, Feb. 2004, pp. 214-219.

J. E. Elias et al., "Target-Decoy Search Strategy for Increased Confidence in Large-Scale Protein Identifications by Mass Spectrometry," Nature Methods, vol. 4, No. 3, Mar. 2007, pp. 207-214.

N. J. Krogan et al., "Global Landscape of Protein Complexes in the Yeast *Saccharomyces cerevisiae*," Nature, vol. 440, Mar. 20, 2006, pp. 637-643.

S. Lenz et al., "In-Search Assignment of Monoisotopic Peaks Improves the Identification of Cross-Linked Peptides," bioRxiv, https://doi.org/10.1101/335851, Aug. 4, 2018, 8 pages.

H. Yu et al.., "Next-Generation Sequencing to Generate Interactome Datasets," Nature Methods, Jun. 2011, 12 pages.

X. Yang et al., "A Public Genome-Scale Lentiviral Expression Library of Human Orfs," Nature Methods, Jun. 2011, 8 pages.

P. Falter-Braun et al., "An Experimentally Derived Confidence Score for Binary Protein-Protein Interactions," Nature Methods, Jan. 2009, 7 pages.

K. Venkatesan et al., "An Empirical Framework for Binary Interactome Mapping," Nature Methods, Jan. 2009, 8 pages.

R. Bomgarden et al., "Optimization of Crosslinked Peptide Analysis on an Orbitrap Fusion Lumos Mass Spectrometer," Thermo Scientific Poster Note 64763, 2016, 3 pages.

A. Leitner et al., "Crosslinking and Mass Spectrometry: An Integrated Technology to Understand the Structure and Function of Molecular Machines," Trends in Biochemical Sciences, vol. 41, No. 1, Jan. 2016, pp. 20-32.

F. Liu et al., "Proteome-Wide Profiling of Protein Assemblies ByCross-Linking Mass Spectrometry," Nature Methods, vol. 12, No. 12, Dec. 2015, 10 pages.

A. Sinz, "Chemical Cross-Linking and Mass Spectrometry to Map Three-Dimensional Protein Structures and Protein-Protein Interactions," Mass Spectrometry Reviews, vol. 25, Feb. 13, 2006, pp. 663-682.

M. J. Meyer et al., "Interactome Insider: A Structural Interactome Browser for Genomic Studies," Nature Methods, vol. 15, No. 2, Feb. 2018, 23 pages.

The UniProt Consortium, "UniProt: The Universal Protein Knowledgebase," Nucleic Acids Research, vol. 45, Nov. 28, 2016, 12 pages.

J. Das et al., "HINT: High-quality Protein Interactomes and Their Applications in Understanding Human Disease," BMC Systems Biology, vol. 6, No. 1, Jul. 2012, 12 pages.

* cited by examiner

FIG. 9A

QYLT[K]ELAK

INTRAPROTEIN CROSSLINK IN E. COLI'S 30S RIBOSOMAL PROTEIN S3 (UNIPROT: P0A7V3)

EFADNLDSDF[K]VR

MaXLinker's FURTHER VALIDATION FILTERS

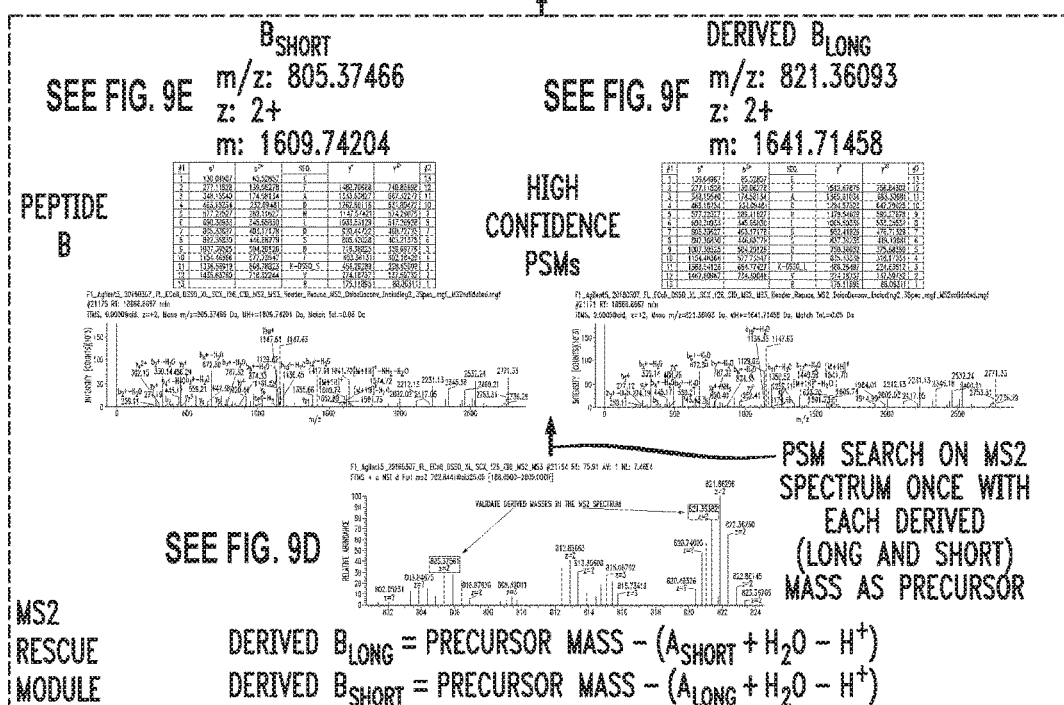

HIGH CONFIDENCE PSMs

PSM SEARCH ON MS2 SPECTRUM ONCE WITH EACH DERIVED (LONG AND SHORT) MASS AS PRECURSOR

MS2 RESCUE MODULE

DERIVED $B_{LONG}$ = PRECURSOR MASS − ($A_{SHORT}$ + $H_2O$ − $H^+$)

DERIVED $B_{SHORT}$ = PRECURSOR MASS − ($A_{LONG}$ + $H_2O$ − $H^+$)

PRECURSOR
m/z: 702.34265
z: 4+
m: 2806.34713

PRECURSOR MASS − ($A_{SHORT}$ + $B_{LONG}$ + $H_2O$ − $H^+$) = 479.12078

PRECURSOR MASS − ($A_{LONG}$ + $B_{SHORT}$ + $H_2O$ − $H^+$) = 479.12750

$B_{SHORT}$
SCAN: 21170
m/z: 565.81036
z: 2+
m: 1130.61345

$B_{LONG}$
SCAN: 21171
m/z: 581.79999
z: 2+
m: 1162.59270

PEPTIDE B   UNINFORMATIVE MS3 SPECTRUM    UNINFORMATIVE MS3 SPECTRUM

SEE FIG. 9B $A_{SHORT}$
SCAN: 21166
m/z: 574.31909
z: 2+
m: 1147.63091

SEE FIG. 9C $A_{LONG}$
SCAN: 21167
m/z: 590.30536
z: 2+
m: 1179.60344

PEPTIDE A

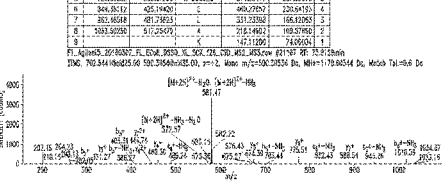

| #1 | b+ | b²⁺ | SEQ. | y+ | y²⁺ | #2 |
|---|---|---|---|---|---|---|
| 1 | 114.09134 | 57.54931 | L | | | 11 |
| 2 | 215.13902 | 108.07315 | T | 1164.64838 | 582.82783 | 10 |
| 3 | 286.17613 | 143.59170 | A | 1063.60070 | 532.30399 | 9 |
| 4 | 423.23504 | 212.12116 | H | 992.56359 | 496.78543 | 8 |
| 5 | 605.34057 | 303.17392 | K-DSSO_S | 855.50468 | 428.25598 | 7 |
| 6 | 719.38350 | 360.19539 | N | 673.39915 | 337.20321 | 6 |
| 7 | 790.42061 | 395.71395 | A | 559.35622 | 280.18175 | 5 |
| 8 | 889.48903 | 445.24815 | V | 488.31911 | 244.66319 | 4 |
| 9 | 990.53671 | 495.77199 | T | 389.25069 | 195.12899 | 3 |
| 10 | 1103.62077 | 552.31402 | L | 288.20302 | 144.60515 | 2 |
| 11 | | | R | 175.11895 | 88.06311 | 1 |

ITMS, 564.3035@cid25.00 639.3652@cid35.00, z=+2, Mono m/z=639.36523 Da, MH+=1277.72319 Da, Match Tol.=0.6 Da

| #1 | b+ | b2+ | b3+ | SEQ. | y+ | y2+ | y3+ | #2 |
|---|---|---|---|---|---|---|---|---|
| 1 | 114.09134 | 57.54931 | 38.70196 | L | | | | 11 |
| 2 | 215.13902 | 108.07315 | 72.38452 | T | 1196.62045 | 598.81387 | 399.54500 | 10 |
| 3 | 286.17613 | 143.59170 | 96.06356 | A | 1095.57278 | 548.29003 | 365.86244 | 9 |
| 4 | 423.23504 | 212.12116 | 141.74987 | H | 1024.53566 | 512.77147 | 342.18340 | 8 |
| 5 | 637.31264 | 319.15996 | 213.10907 | K-DSSO_L | 887.47675 | 444.24201 | 296.49710 | 7 |
| 6 | 751.35557 | 376.18142 | 251.12338 | N | 673.39915 | 337.20321 | 225.13790 | 6 |
| 7 | 822.39269 | 411.69998 | 274.80241 | A | 559.35622 | 280.18175 | 187.12359 | 5 |
| 8 | 921.46110 | 461.23419 | 307.82522 | V | 488.31911 | 244.66319 | 163.44455 | 4 |
| 9 | 1022.50878 | 511.75803 | 341.50778 | T | 389.25069 | 195.12899 | 130.42175 | 3 |
| 10 | 1135.59284 | 568.30006 | 379.20247 | L | 288.20302 | 144.60515 | 96.73919 | 2 |
| 11 | | | | R | 175.11895 | 88.06311 | 59.04450 | 1 |

ITMS, 564.3035@cid25.00 437.2377@cid35.00, z=+3, Mono m/z=437.23773 Da, MH+=1309.69864 Da, Match Tol.=0.6 Da

| #1 | $b^+$ | $b^{2+}$ | $b^{3+}$ | SEQ. | $y^+$ | $y^{2+}$ | $y^{3+}$ | #2 |
|---|---|---|---|---|---|---|---|---|
| 1 | | | | L | | | | 11 |
| 2 | 114.09134 | 57.54931 | 38.70196 | T | 1164.64838 | 582.82783 | 388.88764 | 10 |
| 3 | 215.13902 | 108.07315 | 72.38452 | A | 1063.60070 | 532.30399 | 355.20509 | 9 |
| 4 | 286.17613 | 143.59170 | 96.06356 | H | 992.56359 | 496.78543 | 331.52605 | 8 |
| 5 | 423.23504 | 212.12116 | 141.74987 | K-DSSO_S | 855.50468 | 428.25598 | 285.83974 | 7 |
| 6 | 605.34057 | 303.17392 | 202.45171 | N | 673.39915 | 337.20321 | 225.13790 | 6 |
| 7 | 719.38350 | 360.19539 | 240.46602 | A | 559.35622 | 280.18175 | 187.12359 | 5 |
| 8 | 790.42061 | 395.71395 | 264.14506 | V | 488.31911 | 244.66319 | 163.44455 | 4 |
| 9 | 889.48903 | 445.24815 | 297.16786 | T | 389.25069 | 195.12899 | 130.42175 | 3 |
| 10 | 990.53671 | 495.77199 | 330.85042 | L | 288.20302 | 144.60515 | 96.73919 | 2 |
| 11 | 1103.62077 | 552.31402 | 368.54511 | R | 175.11895 | 88.06311 | 59.04450 | 1 |

F1_Agilent5_20160303_FL_EColi_DSSO_XL_SCX_f28_CID_MS2_MS3.raw #12707 RT: 51.6336 min
ITMS, 564.3035@cid25.00 426.5806@cid35.00, z=+3, Mono m/z=426.58060 Da, MH+=1277.72724 Da, Match Tol.=0.6 Da TO FIG. 12 cont.

LARGE-SCALE MAPPING OF PROTEIN-PROTEIN INTERACTIONS FROM CROSSLINKING MASS SPECTROMETRY

PRIORITY CLAIM

The present application claims priority to U.S. Provisional Patent Application Ser. No. 62/657,257, filed Apr. 13, 2018, and U.S. Provisional Patent Application Ser. No. 62/746,671, filed Oct. 17, 2018, both entitled "Large-Scale Mapping of Protein-Protein Interactions from Crosslinking Mass Spectrometry," each incorporated by reference herein in its entirety.

FIELD

The field relates generally to information processing, and more particularly to techniques for processing data obtained from mass spectrometry.

BACKGROUND

Various techniques are known for analyzing mass spectrometry data in order to identify protein-protein interactions. However, such conventional techniques suffer from a number of significant drawbacks, such as low efficiency in identification of relevant crosslinks and high rates of false positives. Accordingly, a need exists for improved techniques for analysis of mass spectrometry data.

SUMMARY

Illustrative embodiments provide improved techniques for large-scale mapping of protein-protein interactions from crosslinking mass spectrometry. For example, some illustrative embodiments provide techniques for crosslinking of proteins across multiple levels of mass spectrometry data. A given such embodiment can be configured to implement integrative analysis utilizing mass spectrometry data comprising multiple levels of mass spectrometry spectra (e.g., MS1, MS2 and MS3 levels). These and other embodiments perform large-scale protein-protein interaction mapping with substantially higher efficiency and significantly lower rates of false positives than conventional techniques.

In one embodiment, a processing platform comprises one or more processing devices each including at least one processor coupled to a memory. The processing platform is configured to implement a crosslink identification and validation algorithm for processing multiple levels of mass spectrometry data in order to identify and validate protein-protein interactions within the mass spectrometry data. In conjunction with execution of the crosslink identification and validation algorithm, the processing platform is further configured to obtain mass spectrometry spectra for each of the multiple levels, to apply a header matching filter to identify at least one potential crosslink relating one or more first level spectra and one or more second level spectra utilizing a plurality of third level spectra, and to apply one or more mass validation filters to identify whether or not the potential crosslink is a valid crosslink. Responsive to the potential crosslink being identified as a valid crosslink by each of the one or more mass validation filters, the processing platform is further configured to generate a confidence score for the valid crosslink, and to take one or more automated actions based at least in part on the valid crosslink and its confidence score. For example, the one or more automated actions can be carried out as part of a rigorous machine learning based approach.

The processing platform may be configured to iterate operations of the crosslink and validation algorithm in order to identify and validate a plurality of crosslinks based on respective different sets of mass spectrometry data.

The multiple levels of mass spectrometry data illustratively comprise MS1, MS2 and MS3 levels of mass spectrometry data comprising respective MS1, MS2 and MS3 spectra, although other types of multi-level mass spectrometry data can be used in other embodiments.

The header matching filter may be configured to identify a plurality of MS3 spectra having a common header, and to identify the potential crosslink based at least in part on the identified MS3 spectra having the common header. The header matching filter in some embodiments determines the common header based at least in part on precursor mass and charge state entries of headers of the MS1, MS2 and MS3 spectra. The header matching filter is illustratively configured to relate the identified MS3 spectra to their corresponding MS1 and MS2 spectra.

The one or more mass validation filters illustratively comprise at least one of a mass matching validation filter, and a mass validation filter based at least in part on peptide spectrum match (PSM) data. Some embodiments are therefore configured to include both the mass matching validation filter and the mass validation filter based at least in part on PSM data.

As indicated previously, these and other embodiments can provide significant advantages relative to conventional approaches. For example, some embodiments achieve improved efficiency, reduced false positives and other performance enhancements relative to conventional approaches.

These and other embodiments of the invention include but are not limited to systems, methods, apparatus, processing devices, integrated circuits, and processor-readable storage media having software program code embodied therein.

BRIEF DESCRIPTION OF THE FIGURES

FIGS. 9A-9F and 10A-10H show examples of the operation of an MS2 rescue module in the process workflow of FIG. 8.

DETAILED DESCRIPTION

Embodiments of the invention can be implemented, for example, in the form of information processing systems comprising one or more processing platforms each having at least one computer, server or other processing device. Illustrative embodiments of such systems will be described in detail herein. It should be understood, however, that embodiments of the invention are more generally applicable to a wide variety of other types of information processing systems and associated computers, servers or other processing devices or other components. Accordingly, the term "information processing system" as used herein is intended to be broadly construed so as to encompass these and other arrangements.

Figure 1:
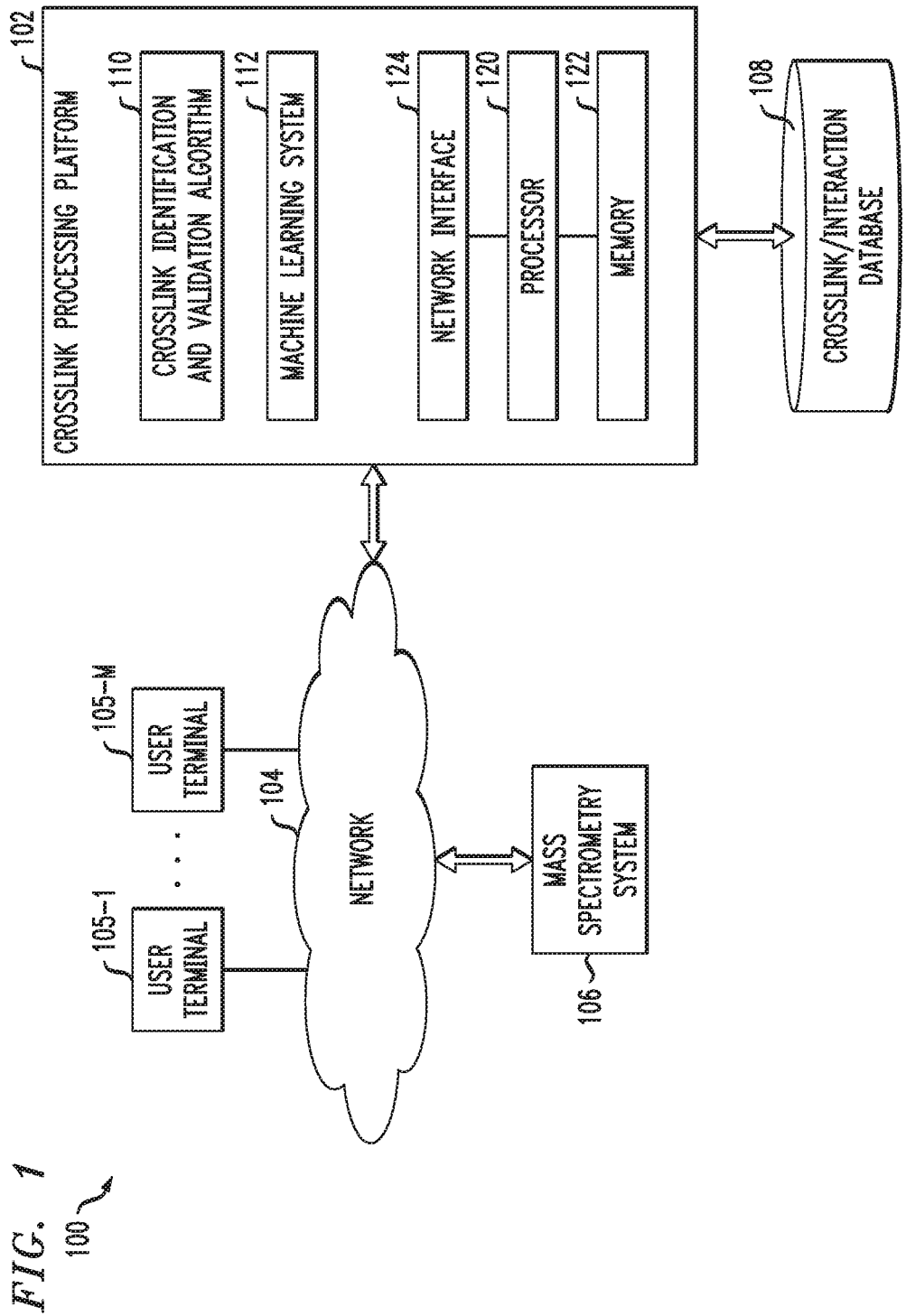
FIG. 1 is a block diagram of an information processing system that incorporates functionality for large-scale mapping of protein-protein interactions from crosslinking mass spectrometry in an illustrative embodiment.

FIG. 1 shows an information processing system 100 implementing functionality for large-scale mapping of protein-protein interactions from crosslinking mass spectrometry in an illustrative embodiment. The system 100 comprises a crosslink processing platform 102 coupled to a network 104. Also coupled to the network 104 are user terminals 105-1, . . . 105-M and a mass spectrometry system 106. The crosslink processing platform 102 is configured to utilize a crosslink/interaction database 108. Such a database illustratively stores crosslinks and/or associated interaction information.

The crosslink processing platform 102 implements at least one crosslink identification and validation algorithm 110 and at least one machine learning system 112.

The crosslink identification and validation algorithm 110 processes multiple levels of mass spectrometry data in order to identify and validate protein-protein interactions within the mass spectrometry data. The machine learning system 112 adjusts various weights and other parameters associated with crosslinks identified and validated by the algorithm 110 in order to optimize the operation of the algorithm 110.

In conjunction with execution of the crosslink identification and validation algorithm 110, the crosslink processing platform 102 obtains mass spectrometry spectra for each of the multiple levels, applies a header matching filter to identify at least one potential crosslink relating one or more first level spectra and one or more second level spectra utilizing a plurality of third level spectra, and applies one or more mass validation filters to identify whether or not the potential crosslink is a valid crosslink.

Responsive to the potential crosslink being identified as a valid crosslink by each of the one or more mass validation filters, the crosslink processing platform 102 generates a confidence score for the valid crosslink, and takes one or more automated actions based at least in part on the valid crosslink and its confidence score. Such automated actions in some embodiments comprise automated actions taken in conjunction with optimizations performed using the machine learning system 112.

A more detailed example of a set of processing operations of one possible implementation of the crosslink identification and validation algorithm 110 will be described below in conjunction with the flow diagram of FIG. 4. Another example implementation will be described below in conjunction with the flow diagram of FIG. 8. These are only examples, and numerous alternative arrangements are possible.

The crosslink processing platform 102 may be configured to iterate operations of the crosslink and validation algorithm 110 in order to identify and validate a plurality of crosslinks based on respective different sets of mass spectrometry data.

The multiple levels of mass spectrometry data utilized by the algorithm 110 illustratively comprise MS1, MS2 and MS3 levels of mass spectrometry data comprising respective MS1, MS2 and MS3 spectra, although other types of multi-level mass spectrometry data can be used in other embodiments.

The header matching filter may be configured to identify a plurality of MS3 spectra having a common header, and to identify the potential crosslink based at least in part on the identified MS3 spectra having the common header. The header matching filter in some embodiments determines the common header based at least in part on precursor mass and charge state entries of headers of the MS1, MS2 and MS3 spectra. The header matching filter is illustratively configured to relate the identified MS3 spectra to their corresponding MS1 and MS2 spectra.

In alternative embodiments, the header matching filter may be configured to identify consecutive MS3 spectra having a common header, although it is to be appreciated that identification of consecutive MS3 spectra is not required.

The one or more mass validation filters illustratively comprise at least one of a mass matching validation filter, and a mass validation filter based at least in part on peptide spectrum match (PSM) data. Some embodiments are therefore configured to include both the mass matching validation filter and the mass validation filter based at least in part on PSM data. The embodiments of FIGS. 4 and 8 to be described below are examples of such embodiments, although it is to be appreciated that other embodiments can implement different arrangements of header matching filters and/or mass validation filters, as well as additional or alternative filters for validating potential crosslinks in the crosslink processing platform 102.

Although the crosslink identification and validation algorithm 110 and the machine learning system 112 are both shown as being implemented on crosslink processing platform 102 in the present embodiment, this is by way of illustrative example only. In other embodiments, the components 110 and 112 can each be implemented on a separate processing platform. A given such processing platform is assumed to include at least one processing device comprising a processor coupled to a memory. Examples of such processing devices include computers, servers or other processing devices arranged to communicate over a network. Storage devices such as storage arrays or cloud-based storage systems used for implementation of crosslink/interaction database 108 are also considered "processing devices" as that term is broadly used herein.

It is also possible that at least portions of other system elements such as the mass spectrometry system 106 can be implemented as part of the crosslink processing platform 102, although shown as being separate from the crosslink processing platform 102 in the figure.

The crosslink processing platform 102 is configured for bidirectional communication with the user terminals 105 over the network 104. For example, images, displays and other outputs generated by the crosslink processing platform 102 can be transmitted over the network 104 to user terminals 105 such as, for example, a laptop computer, tablet computer or desktop personal computer, a mobile telephone, or another type of computer or communication device, as well as combinations of multiple such devices. The crosslink processing platform 102 can also receive input data from the mass spectrometry system 106 or other data sources, such as PSM data sources, over the network 104.

The network 104 can comprise, for example, a global computer network such as the Internet, a wide area network (WAN), a local area network (LAN), a satellite network, a telephone or cable network, a cellular network, a wireless network implemented using a wireless protocol such as WiFi or WiMAX, or various portions or combinations of these and other types of communication networks.

Examples of automated actions that may be taken in the crosslink processing platform 102 responsive to a potential crosslink being identified as a valid crosslink include reporting the valid crosslink and its confidence score over network 104 to at least one of the user terminals 105, generating at least a portion of at least one output display comprising at least one of the valid crosslink and its confidence score for presentation to at least one of the user terminals 105, generating an alert based at least in part on the valid crosslink and its confidence score for delivery to at least one of the user terminals 105 over the network 104, and storing the valid crosslink and its confidence score in the crosslink/interaction database 108.

Additional or alternative automated actions may be taken in other embodiments. For example, as indicated previously, automated actions can include actions performed by the machine learning system 112 in optimizing or otherwise controlling one or more features or other aspects of a crosslink identification process.

The crosslink processing platform 102 in the present embodiment further comprises a processor 120, a memory 122 and a network interface 124. The processor 120 is assumed to be operatively coupled to the memory 122 and to the network interface 124 as illustrated by the interconnections shown in the figure.

The processor 120 may comprise, for example, a microprocessor, an application-specific integrated circuit (ASIC), a field-programmable gate array (FPGA), a central processing unit (CPU), an arithmetic logic unit (ALU), a digital signal processor (DSP), or other similar processing device component, as well as other types and arrangements of processing circuitry, in any combination.

As a more particular example, in some embodiments, the processor 120 comprises one or more graphics processor integrated circuits. Such graphics processor integrated circuits are illustratively implemented in the form of one or more graphics processing units (GPUs). Accordingly, in some embodiments, system 100 is configured to include a GPU-based processing platform.

The memory 122 stores software program code for execution by the processor 120 in implementing portions of the functionality of the crosslink processing platform 102. For example, at least portions of the functionality of crosslink identification and validation algorithm 110 and machine learning system 112 can be implemented using program code stored in memory 122.

A given such memory that stores such program code for execution by a corresponding processor is an example of what is more generally referred to herein as a processor-readable storage medium having program code embodied therein, and may comprise, for example, electronic memory such as SRAM, DRAM or other types of random access memory, flash memory, read-only memory (ROM), magnetic memory, optical memory, or other types of storage devices in any combination.

Articles of manufacture comprising such processor-readable storage media are considered embodiments of the invention. The term "article of manufacture" as used herein should be understood to exclude transitory, propagating signals.

Other types of computer program products comprising processor-readable storage media can be implemented in other embodiments.

In addition, embodiments of the invention may be implemented in the form of integrated circuits comprising processing circuitry configured to implement processing operations associated with one or both of the crosslink identification and validation algorithm 110 and the machine learning system 112 as well as other related functionality.

The network interface 124 is configured to allow the crosslink processing platform 102 to communicate over one or more networks with other system elements, and may comprise one or more conventional transceivers.

It is to be appreciated that the particular arrangement of components and other system elements shown in FIG. 1 is presented by way of illustrative example only, and numerous alternative embodiments are possible. For example, other embodiments of information processing systems can be configured to provide crosslink identification functionality of the type disclosed herein.

Figure 2:
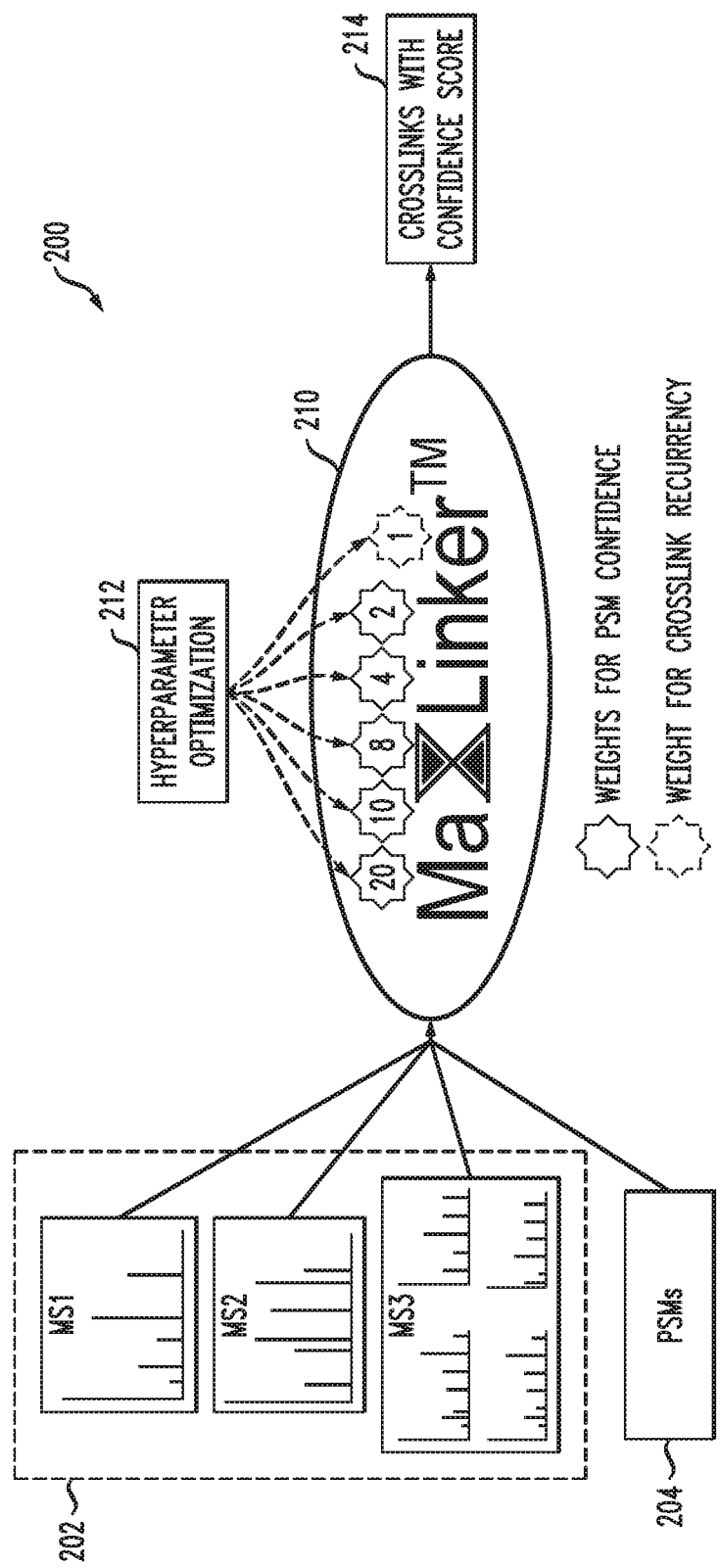
FIG. 2 illustrates the operation of an example implementation of a crosslink identification and validation algorithm of the FIG. 1 system in one embodiment.

FIG. 2 illustrates the operation of an example implementation 200 of crosslink identification and validation algorithm 110 in the crosslink processing platform 102 in one embodiment.

The implementation 200 receives as its input 202 multiple levels of mass spectrometry data, including MS1, MS2 and MS3 levels of mass spectrometry data comprising respective MS1, MS2 and MS3 spectra.

Figure 3:
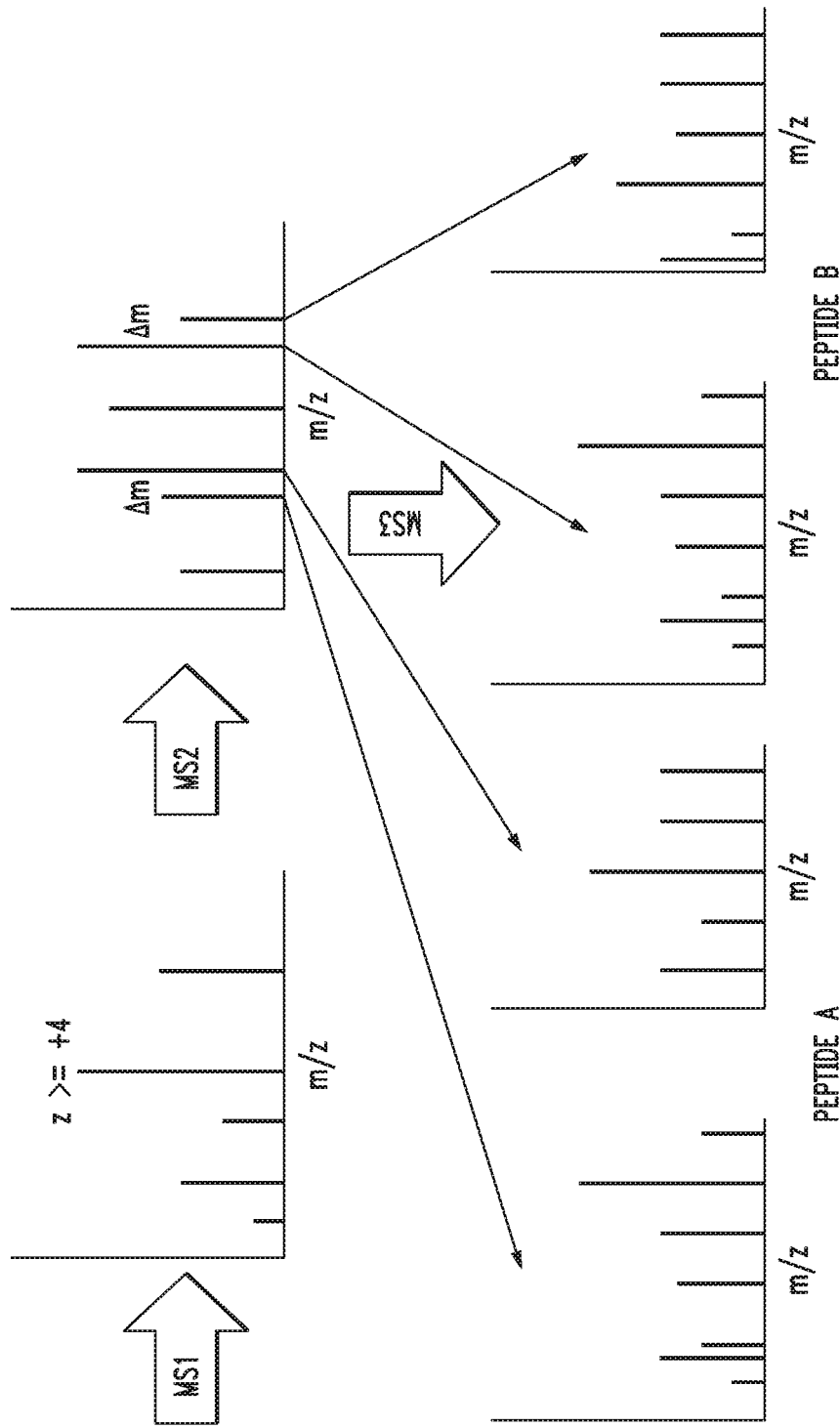
FIG. 3 illustrates possible relationships between different levels of mass spectrometry spectra in an illustrative embodiment.

Examples of possible relationships between MS1, MS2 and MS3 levels of mass spectrometry spectra in the input 202 of the implementation 200 are shown in FIG. 3, and include pairs of MS3 spectra for respective peptides denoted as Peptide A and Peptide B. FIG. 3 more particularly illustrates an example of what is also referred to herein as an MS2-MS3 approach to generating multiple levels of mass spectrometry spectra.

These and other inputs referred to herein are in some cases in the form of .mgf files, although other file formats and mass spectrometry data types may be used in other embodiments. Additional input received by the implementation 200 includes PSM data 204 illustratively comprising one or more lists of PSMs, illustratively obtained from a SEQUEST search or other PSM data source. It is to be appreciated that use of a SEQUEST search or any other particular type of PSM data source is not a requirement, and alternative arrangements can be used to obtain PSM data. All references herein to SEQUEST searches, or other particular types of tools, software programs or databases, should be considered non-limiting.

In some embodiments, the crosslink identification and validation algorithm 110 is more particularly implemented as a MaXLinker™ algorithm 210 that can identify crosslinks utilizing mass spectrometry data obtained from one or more MS2-MS3 crosslinking mass spectrometry (XLMS) experiments.

The MaXLinker™ embodiments disclosed herein can generally be utilized with virtually any type of MS-cleavable crosslinker, although some implementations are described in the context of a particular MS-cleavable crosslinker, such as disuccinimidyl sulfoxide (DSSO). Other embodiments can be adapted in a straightforward manner for use with use with other types of MS-cleavable crosslinkers, as will be appreciated by those skilled in the art. The illustrative embodiments should therefore not be viewed as being limited to use with DSSO or any other particular MS-cleavable crosslinker. Such MS-cleavable crosslinkers are also referred to herein as simply "linkers."

Figure 4:
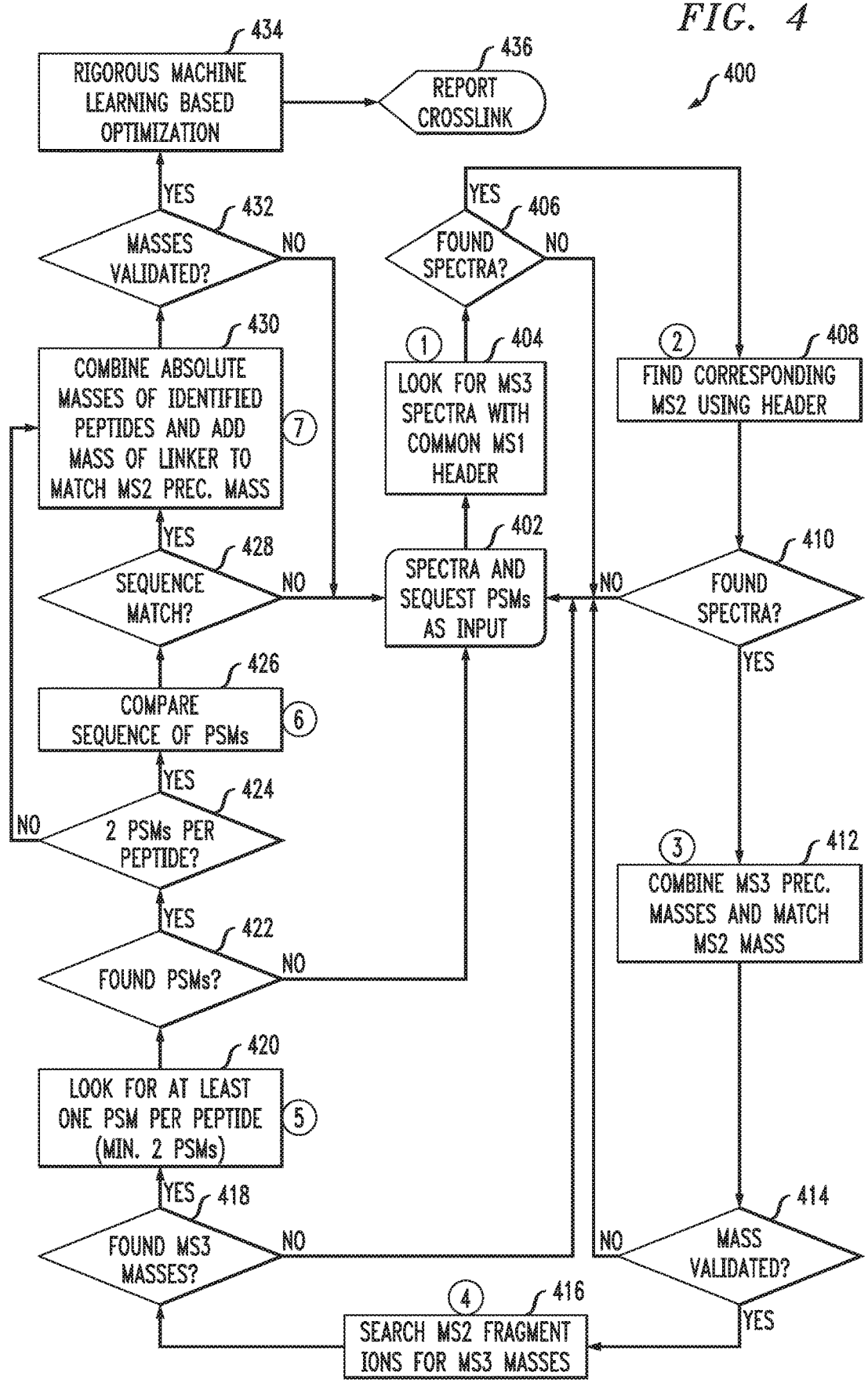
FIG. 4 is a flow diagram showing a process workflow of an example crosslink identification and validation algorithm in an illustrative embodiment.
Figure 8:
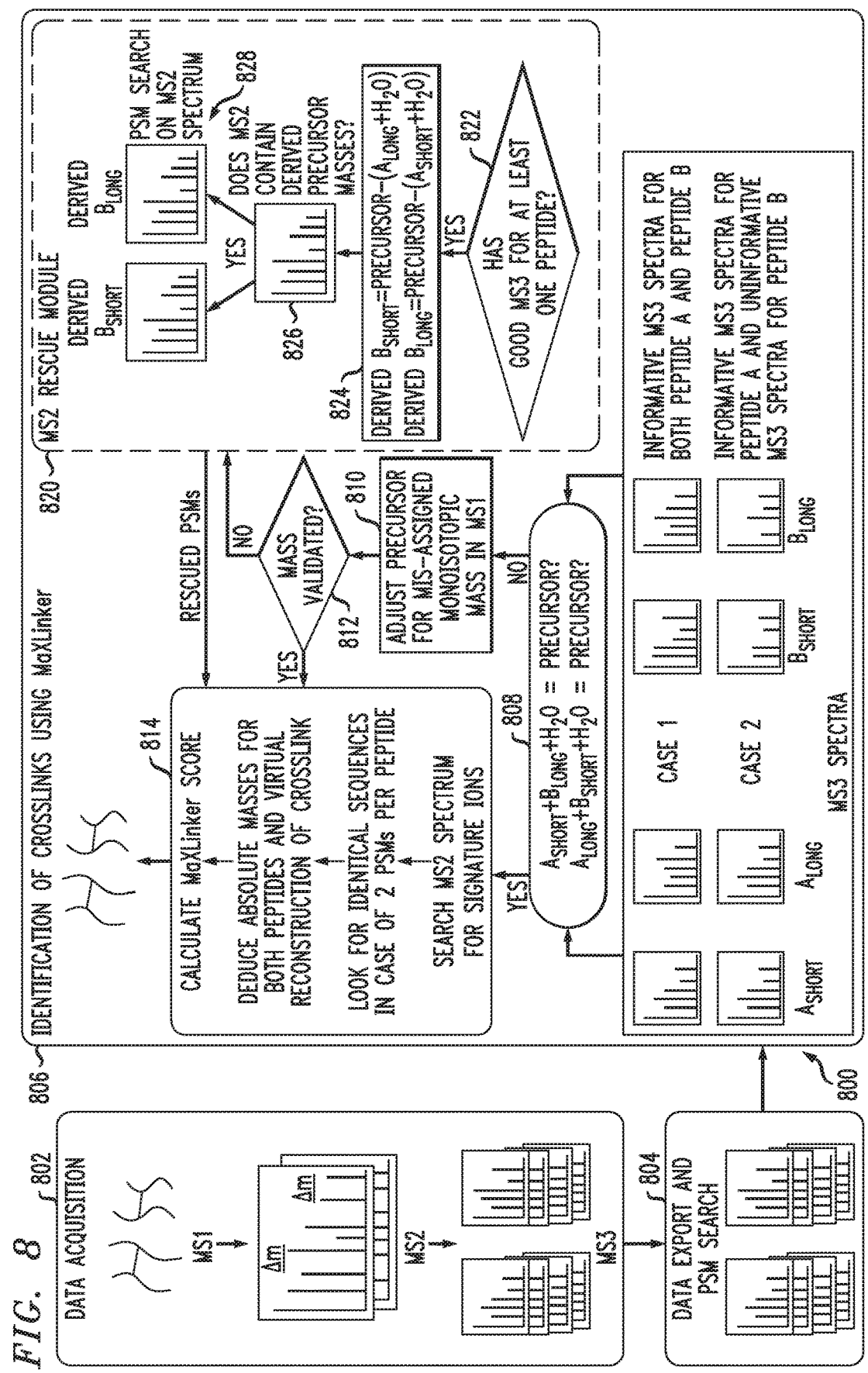
FIG. 8 is a flow diagram showing a process workflow of another example crosslink identification and validation algorithm in an illustrative embodiment.

The MaXLinker™ algorithm 210 in illustrative embodiments is assumed to implement one or more iterations of the crosslink identification and validation algorithm of FIG. 4 and/or the crosslink identification and validation algorithm of FIG. 8.

Advantageously, the MaXLinker™ algorithm 210 can efficiently identify high quality crosslinks with high precision, and a minimal number of false positives. This embodiment incorporates rigorous filters at various steps to eliminate potential false positives, as illustrated in the flow diagrams of FIGS. 4 and 8.

The implementation 200 includes functionality for hyperparameter optimization 212, illustratively via the machine learning system 112. Such functionality is used to generate appropriate weights for PSM confidence and crosslink recurrency for use by the MaXLinker™ algorithm 210 in generating outputs 214 comprising valid crosslinks having respective confidence scores.

For example, the weights for PSM confidence illustratively include weights that are assigned for each PSM based on the confidence with which that PSM was identified, which is inversely proportional to the q-value referred to elsewhere herein. Accordingly, a high confidence PSM will be assigned a higher weight as opposed to a medium confidence PSM or a low confidence PSM.

The weight for crosslink recurrency generally accounts for the number of times a given peptide pair is identified in a full search and is used to boost the confidence score for the corresponding crosslink in a manner that is directly proportional to the number of times that peptide pair was identified. In other words, if a given peptide pair is identified multiple times (i.e., is recurrent in the search), there is a very good chance that the identification is a true positive, with the likelihood of such a true positive identification increasing with the number of times the peptide pair was identified.

These particular weighting arrangements are examples only, and other types of weightings can be used.

Referring now to FIG. 4, a process 400 is shown that represents one possible implementation of the crosslink identification and validation algorithm 110 in the system 100 of FIG. 1, namely, the MaXLinker™ algorithm 210. The process 400 comprises steps 402 through 436, which are illustratively performed by the crosslink processing platform 102 utilizing one or more software programs stored in memory 122 and executed by processor 120. It is to be appreciated that other embodiments can include additional or alternative steps implementing other filtering arrangements for identification and validation of crosslinks using algorithm 110 of the crosslink processing platform 102.

In step 402, input data comprising mass spectrometry spectra and associated PSMs is obtained. Such data is illustratively obtained at least in part from mass spectrometry system 106 or other sources of mass spectrometry data, such as PSM data sources. The mass spectrometry data is assumed to include MS1, MS2 and MS3 levels of mass spectrometry data comprising respective MS1, MS2 and MS3 spectra, of the type illustrated in the MS1, MS2 and MS3 examples of FIG. 3.

In step 404, the crosslink identification and validation algorithm looks for MS3 spectra with a common MS1 header.

In step 406, a determination is made as to whether or not any such MS3 spectra with a common MS1 header were found. If no such spectra were found, the process returns to step 402 to obtain additional input data for processing. Otherwise, the process moves to step 408.

In step 408, the process attempts to find corresponding MS2 spectra utilizing the header.

In step 410, a determination is made as to whether or not any such corresponding MS2 spectra were found. If no such spectra were found, the process returns to step 402 to obtain additional input data for processing. Otherwise, the process moves to step 412.

In step 412, the process attempts to validate the MS3 spectra by crosschecking the ability of multiple combinations of their precursor masses to reconstitute the precursor mass of the crosslink.

In step 414, a determination is made as to whether or not the mass has been validated. If the mass is not validated, the process returns to step 402 to obtain additional input data for processing. Otherwise, the process moves to step 416.

In step 416, the process attempts to confirm the presence of the MS3 masses in their corresponding MS2 spectra by searching MS2 fragment ions for the MS3 masses.

In step 418, a determination is made as to whether or not the MS3 masses were found. If the MS3 masses were not found, the process returns to step 402 to obtain additional input data for processing. Otherwise, the process moves to step 420.

In step 420, a PSM list is parsed in order to identify at least one PSM per peptide and a total of at least two PSMs. These are the candidate peptides for the crosslink.

In step 422, a determination is made as to whether or not the requisite PSMs were found. If the requisite PSMs were not found, the process returns to step 402 to obtain additional input data for processing. Otherwise, the process moves to step 424.

In step 424, a determination is made as to whether or not there are at least two PSMs per peptide. If there are at least two PSMs per peptide, the process moves to step 426. Otherwise the process skips steps 426 and 428 and moves to step 430.

In step 426, sequences of PSMs are compared.

In step 428, a determination is made as to whether or not the sequences of PSMs match. If the sequences of PSMs do not match, the process returns to step 402 to obtain additional input data for processing. Otherwise, the process moves to step 430.

In step 430, the process performs a further validation step to confidently assign the crosslink by reconstituting the crosslink from the identified peptide sequences. More particularly, the process combines absolute masses of the identified peptides and adds the mass of the linker in an attempt to match the MS2 precursor mass.

The term "absolute mass" in this context and elsewhere herein illustratively refers to the theoretical mass of a peptide without any modifications, such as those associated with the "long" or "short" arms of the linker. The further validation performed in step 430 illustratively derives the theoretical mass of the full reconstituted crosslink from the theoretical masses of its individual components (e.g., peptide+linker+water) in conjunction with attempting to match it with the MS2 precurser mass.

In step 432, a determination is made as to whether or not the combined masses have been validated. If the combined masses are not validated, the process returns to step 402 to obtain additional input data for processing. Otherwise, the process moves to step 434.

In step 434, a rigorous machine learning based optimization is performed. Additional details regarding machine learning based functionality of the system 100 will be described below in conjunction with FIG. 7.

In step 436, the validated crosslink is reported. Although not illustrated in the figure, an additional return from step 436 to step 402 may be included, in order to implement further iterations of the process 400 so as to identify additional crosslinks through processing of MS1, MS2 and MS3 spectra and associated PSMs.

The identified crosslink may be reported in step 436 with a corresponding confidence score. The confidence score is illustratively computed as follows:

$$\text{Confidence Score} = (\Sigma q_{rescaled} \times W_{XL}) + N \qquad (1)$$

where $q_{rescaled}$ denotes rescaled q-value, $W_{XL}$ denotes weight for crosslink PSM confidence, and N denotes number of recurrences. Other types of confidence scores can be used in other embodiments.

The q-value in some embodiments can be obtained using a software program known as Percolator, although the use of Percolator is not a requirement of any particular embodiment, and q-values or other statistical measures can be obtained in other ways.

By way of example, the q-value in some embodiments is a value falling within a specified range, such as a range of 0.00 to 0.05, with lower values being better than higher values. In order to incorporate a q-value of this type into the above-described MaXLinker™ confidence score, the q-value can be rescaled by subtracting it from 1. In such an arrangement, if the q-value is 0.003, then the rescaled q-value is 0.997 (i.e., 1-0.003). As a result, the rescaled q-values would range from 0.95 to 1.00, with higher values being better than lower values. Other types of rescaling can be used.

The MaXLinker™ algorithm as illustrated in the flow diagram of FIG. 4 implements a header matching filter, a mass matching validation filter, and a mass validation filter based at least in part on PSM data.

Steps 404 to 410 correspond generally to an example implementation of the header matching filter, and are illustratively configured to tether or otherwise relate the MS3 spectra to the corresponding MS2 and MS1 spectra using, for example, the precursor mass and charge state in the header.

Steps 412-418 correspond generally to an example implementation of the mass matching validation filter, and are illustratively configured to validate the MS3 spectra by crosschecking the ability of multiple combinations of their precursor masses to reconstitute the precursor mass of the crosslink, and to confirm the presence of those precursor masses in the corresponding MS2 spectra.

Steps 420-432 correspond generally to an example implementation of the mass validation filter based at least in part on PSM data. This filter is illustratively configured to parse the PSM list to find the candidate peptides for the crosslink in steps 420-422, to compare sequences of PSMs if such sequences exist in steps 424-428, and to provide further validation to confidently designate the crosslink as a valid crosslink by reconstituting the crosslink from the identified peptide sequences in steps 430-432.

Again, the particular process steps illustrated in the FIG. 4 embodiment are presented by way of illustrative example only, and additional or alternative process steps can be used in other embodiments. For example, different arrangements of header matching and mass validation filters can be used. Another detailed example of one possible implementation of the crosslink identification and validation algorithm 110 will be described below in conjunction with the illustrative embodiment of FIG. 8.

Figure 5:
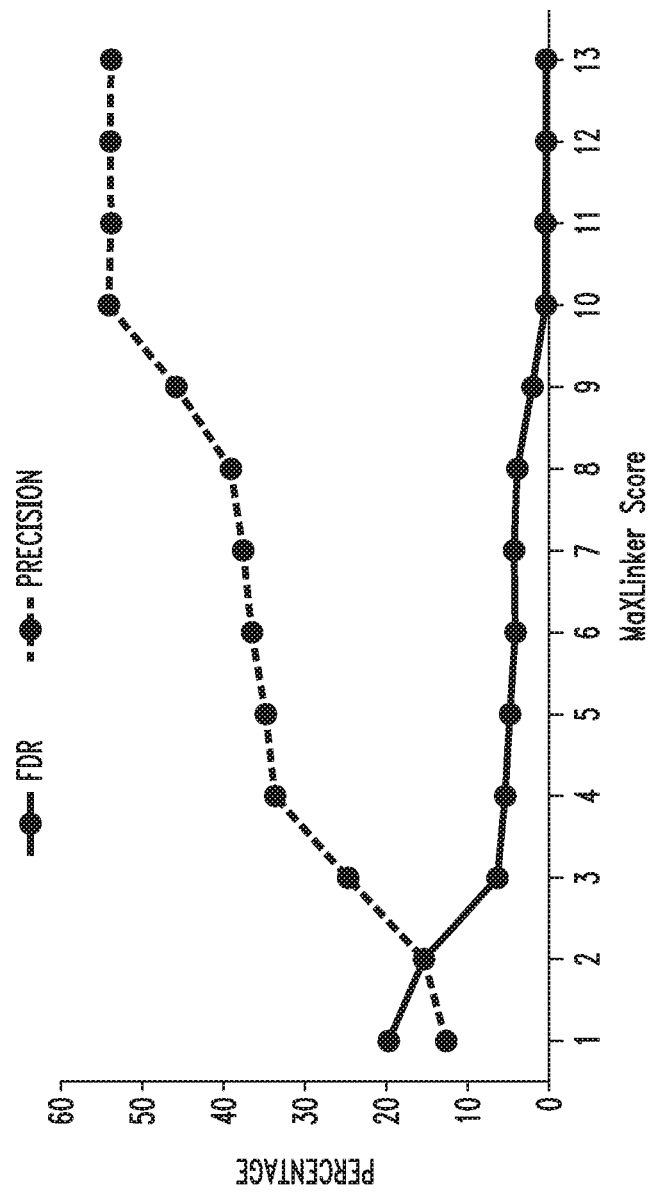
FIG. 5 is a graphical plot showing false discovery rate (FDR) and precision as a function of confidence score generated using the example crosslink identification and validation algorithm of FIG. 4.

The graphical plot in FIG. 5 illustrates the robustness of the confidence scores generated by the MaXLinker™ algorithm in the above-described implementation of FIG. 4. In FIG. 5, false discovery rate (FDR) and precision are both plotted in terms of percentage as a function of the MaXLinker™ confidence score. It is apparent that the MaXLinker™ confidence score can be used to determine an optimum set of high quality crosslinks at high precision and with low numbers of false positives. The scores in this plot were based on mass spectrometry data comprising a set of 12 MS2-MS3 XLMS fractions from a K562 cell line.

The MaXLinker™ algorithm in the present embodiment utilizes a target-decoy strategy to establish the FDR. More particularly, a concatenated database comprising target and decoy sequences is used for the PSM search and the FDR is calculated using the equation:

$$\text{FDR} = FP/(FP+TP) \qquad (2)$$

where FP denotes false positive hits and TP denotes true positive hits. For crosslink identification, TP represents the number of crosslinks with both of the linked peptides from the target database and FP represents the number of crosslinks with at least one of the linked peptides from the decoy database.

The identified crosslinks were annotated as "interprotein" if neither of the linked peptides were derived from a common protein sequence, with exception for those instances where both the linked peptides from a common protein were identical or one of them was a complete subset of the other and the peptide occurred only once in the protein sequence. Crosslinks that did not satisfy these criteria were annotated as "intraprotein."

Precision in these and other embodiments is illustratively defined as the fraction of the identified interprotein crosslinks that are previously known protein-protein interactions. It can be derived using the following equation:

$$\text{Precision}(\%) = \frac{\text{Number of true positives}}{\text{Total number of positives}} \times 100 \qquad (3)$$

where "total number of positives" denotes all the identified interprotein crosslinks, and "number of true positives" denotes those of the identified interprotein crosslinks that are from known protein-protein interactions.

We have found that conventional XLMS evaluation measures can suffer from massive underestimation of false positives in case of the interprotein crosslinks, which are key for inferring novel protein-protein interactions and modeling 3D structure for functional complexes. For example, some conventional evaluation measures selectively pre-filter only highly likely true positives for the distance-based validation, ignoring the potential false positives. The precision measure defined in Equation (3) above advantageously overcomes these and other drawbacks of conventional XLMS evaluation measures, leading to improved crosslink identification performance in illustrative embodiments. For example, in some embodiments, the precision measure of Equation (3) is used in machine learning system 112 to drive automated optimization of crosslink identification.

Other techniques can be used to determine confidence score, FDR and/or precision in other embodiments. The particular arrangements of Equations (1), (2) and (3) should therefore be considered examples.

Figure 6:
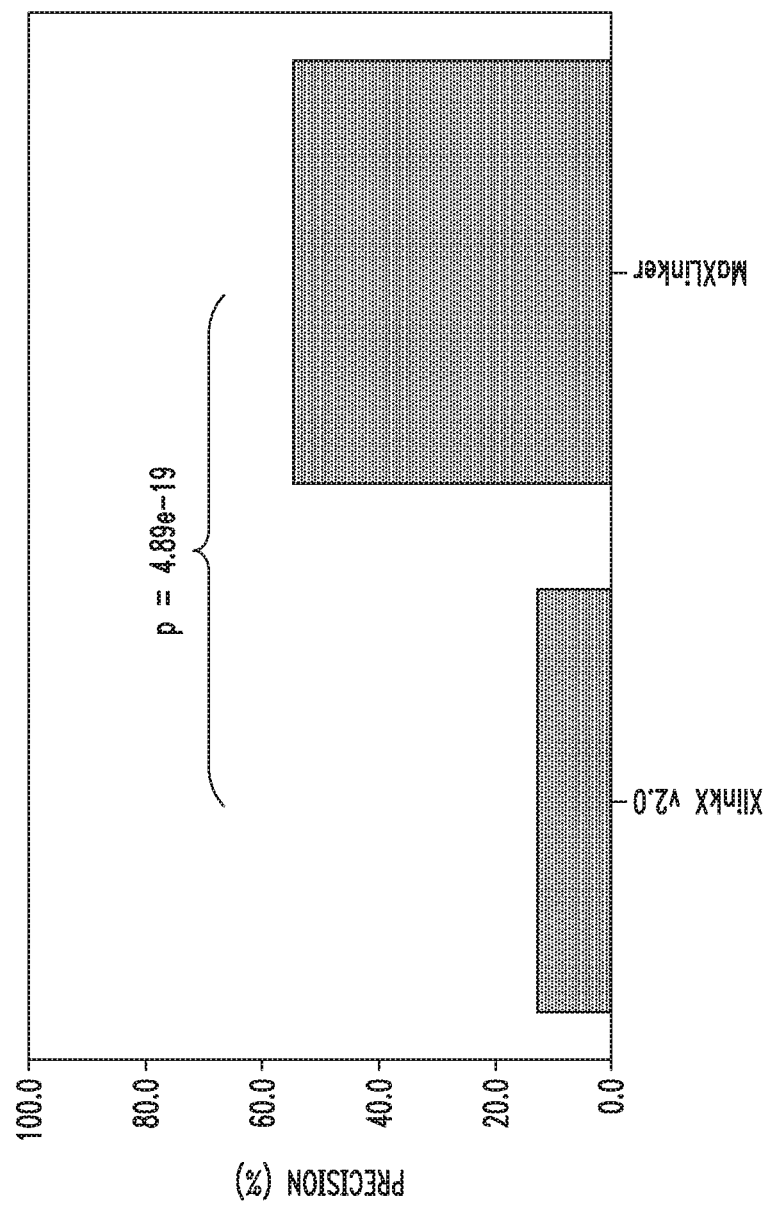
FIG. 6 is a graphical plot comparing performance of the example crosslink identification and validation algorithm of FIG. 4 to that of a conventional approach.

Referring now to FIG. 6, a graphical plot is shown comparing performance of the MaXLinker™ algorithm to that of a conventional approach, again utilizing the above-noted set of 12 MS2-MS3 XLMS fractions from the K562 cell line. The conventional approach in this example is implemented using XlinkX v2.0 software, described in F. Liu et al., "Optimized fragmentation schemes and data analysis strategies for proteome-wide cross-link identification," Nature Communications, 2017, 8:15473. The figure compares the performance of MaXLinker™ with that of XlinkX v2.0 in terms of precision in percent. It is apparent from the figure that MaXLinker™ can identify crosslinks with a significantly higher precision than XlinkX v2.0 when both approaches are operating on the same set of 12 MS2-MS3 XLMS fractions from the K562 cell line.

Similar advantages were exhibited in other experiments comparing the performance of MaXLinker™ with that of XlinkX v2.0 for other mass spectrometry data sets. For example, when utilized to process mass spectrometry data comprising six *E. coli* fractions from the above-cited F. Liu et al. reference, XlinkX v2.0 identified 551 crosslinks at a precision of 33.3%, while MaXLinker™ identified 427 crosslinks at a precision of 70.8%.

Such advantages in the present embodiment are believed to be attributable at least in part to the fact that MaXLinker™ starts its search for potential crosslinks by examining MS3 spectra, while also implementing other stringent filters in its exemplary workflow as illustrated in FIG. 4, including validation based on theoretical reconstruction of the potential crosslink at various stages, and strict sequence-matching criteria when multiple PSMs were found for each of the crosslinked peptides. These and other features allow MaXLinker™ to identify crosslinks with high precision while also efficiently eliminating false positives.

As mentioned previously, MaXLinker™ and other implementations of crosslink identification and validation algorithm 110 can regularly optimize their respective scoring criteria through utilization of the machine learning system 112.

One possible implementation 700 of machine learning functionality utilizing machine learning system 112 of crosslink processing platform 102 will now be described with reference to FIG. 7. More particularly, the implementation 700 illustrates a workflow for MaXLinker™ machine learning based probability scoring functionality as performed by the machine learning system 112.

In this example workflow, crosslinks 702 generated by the crosslink identification and validation algorithm 110 are randomly split by operation 703 into a training set 704-1 and testing set 704-2. A benchmarking operation 705 using positive-unlabeled learning is then performed using the training set 704-1.

This operation illustratively utilizes, by way of example only, the continually-growing set of known protein-protein interactions in the HINT database, described in J. Das et al., "HINT: High-quality protein interactomes and their applications in understanding human disease," BMC Systems Biology, 2012 Jul. 6(1):92, although use of HINT or any other particular database should not be viewed as a requirement. Numerous alternative implementations of crosslink/interaction database 108 or other types of public or private databases can therefore be used in illustrative embodiments.

The resulting benchmarked crosslinks are applied to a multilayer perceptron 706, illustratively implementing a type of neural network. The multilayer perceptron 706 generates probability scores 708 for the respective ones of the crosslinks. The probability scores 708 are utilized in applying a benchmarking operation 709 using positive-unlabeled learning to the testing set 704-2.

Such an arrangement may be viewed as implementing a feedback loop in which known interactions from the HINT database or other type of database are used to identify high quality crosslinks. Novel interactions identified from the interprotein crosslinks are fed back to the database, thus contributing to its growth.

Moreover, the implementation 700 of machine learning system 112 is configured to assign the probability scores 708 to respective ones of the crosslinks based at least in part on knowledge gained from the known interactions using the neural network implemented by the multilayer perceptron 706.

Other types of machine learning functionality implemented using the machine learning system 112 may be used in other embodiments.

Referring now to FIG. 8, another example implementation of the crosslink identification and validation algorithm 110 is shown. This figure illustrates a process 800 that represents another possible implementation of the crosslink identification and validation algorithm 110, and thus another version of the MaXLinker™ algorithm 210. The process 800 comprises steps 802 through 814, which are similar to steps 402 through 436 of the FIG. 4 embodiment, but further includes an MS2 rescue module 820 that, when triggered under certain specified conditions, performs additional steps 822 through 828.

Like the process 400 of FIG. 4, the process 800 is illustratively performed by the crosslink processing platform 102 utilizing one or more software programs stored in memory 122 and executed by processor 120. It is to be appreciated that other embodiments can include additional or alternative steps implementing other filtering arrangements for identification and validation of crosslinks using algorithm 110 of the crosslink processing platform 102.

Step 802 of FIG. 8 is a data acquisition step, and step 804 is a data export and PSM search step. Step 806 then performs identification of crosslinks using the corresponding version of the MaXLinker™ algorithm, illustratively involving execution of at least a subset of steps 808 through 814, and in some cases execution of additional steps 822 through 828 of the MS2 rescue module 820.

In steps 802 and 804, input data comprising mass spectrometry spectra and associated PSMs is obtained for use in step 806. Such data is illustratively obtained at least in part from mass spectrometry system 106 or other sources of mass spectrometry data, such as PSM data sources. The mass spectrometry data is assumed to include MS1, MS2 and MS3 levels of mass spectrometry data comprising respective MS1, MS2 and MS3 spectra, of the type illustrated in the MS1, MS2 and MS3 examples of FIG. 3.

Steps 802 and 804 illustratively represent a pre-processing stage of a processing pipeline provided by the process 800. In some implementations, this pre-processing stage obtains .mgf files with different levels of mass spectrometry (MS) spectra exported using, by way of example only, Proteome Discoverer (PD), along with list of PSMs from SEQUEST search in PD using a concatenated database comprising target and randomized protein sequences. It may further generate one or more .mgf files to be subsequently used for SEQUEST searches or other types of PSM searches. Again, tools such as SEQUEST and PD referred to in the context of illustrative embodiments are not required, and alternative arrangements can be used in place of these particular tools in other embodiments.

Step 806 illustratively represents a crosslink search stage of the processing pipeline provided by the process 800. In some implementations, this crosslink search stage accepts .mgf files with different levels of MS spectra and the list of PSMs from the SEQUEST search as input and performs the search through multiple steps using stringent validation filters of the type previously described.

More particularly, the version of the MaXLinker™ algorithm as illustrated in the flow diagram of FIG. 8 is assumed to implement a header matching filter, a mass matching validation filter, and a mass validation filter based at least in part on PSM data, similar to the corresponding filters of the FIG. 4 embodiment.

For example, a header matching filter in the FIG. 8 embodiment can be configured to tether or otherwise relate the MS3 spectra to the corresponding MS2 and MS1 spectra using, for example, the precursor mass and charge state in the header.

Steps 808-814 correspond generally to example implementations of the mass matching validation filter and the mass validation filter based at least in part on PSM data, similar to those previously described in conjunction with FIG. 4.

The mass matching validation filter is illustratively configured to validate the MS3 spectra by crosschecking the ability of multiple combinations of their precursor masses to reconstitute the precursor mass of the crosslink, and to confirm the presence of those precursor masses in the corresponding MS2 spectra. The mass validation filter based at least in part on PSM data is illustratively configured to parse the PSM list to find the candidate peptides for the crosslink, to compare sequences of PSMs if such sequences exist, and to provide further validation to confidently designate the crosslink as a valid crosslink by reconstituting the crosslink from the identified peptide sequences.

For example, step 808 attempts to validate the MS3 spectra by crosschecking the ability of multiple combinations of their precursor masses to reconstitute the precursor mass of the crosslink. If the validation is successful at this step, the process moves directly to step 814 as indicated. Otherwise, step 810 adjusts the precursor for misassigned monoisotopic mass in MS1, and the mass validation is attempted using the adjusted precursor in step 812. A successful mass validation at step 812 causes the process to move to step 814.

In step 814, multiple operations are performed as indicated in the figure. More particularly, the MS2 spectrum is searched for signature ions, and an attempt is made to find identical sequences in the case of 2 PSMs per peptide. Absolute masses are then deduced for both peptides and virtual reconstruction of the crosslink is performed. This illustratively involves combining absolute masses of the identified peptides and adding the mass of the linker in an attempt to match the MS2 precursor mass. A MaXLinker™ score is then generated in the manner described elsewhere herein, illustratively using Equation (1) above. Other types of confidence scores can be used in other embodiments.

If the mass validation for the adjusted precursor in step 812 is not successful, the MS2 rescue module 820 is triggered. This is an example of the MS2 rescue module 820 is therefore triggered responsive to a failure of the mass matching validation filter to confirm validity of an MS2 precursor mass for the potential crosslink.

Additional or alternative conditions can cause the MS2 rescue module 820 to be triggered for a given potential crosslink. For example, the MS2 rescue module 820 can also be triggered responsive to a failure of the mass validation filter based at least in part on PSM data to obtain reliable PSM data for at least one candidate peptide. Terms such as "reliable" and "reliably identified" as used herein are intended to be broadly construed, so as to refer, by way of example, to PSM data, peptides or other search results that satisfy one or more designated criteria of a particular crosslink search. Such criteria can vary from search to search, and thus may differ in different instances of execution of a MaXLinker™ algorithm. For example, certain reliability criteria to be applied for a given crosslink search can be adjusted by a system user in some embodiments.

In step 822, the MS2 rescue module 820 initially determines if there is at least one peptide reliably identified from corresponding MS3 spectra and terminates its current processing instance if there is no such reliably identified peptide.

Responsive to there being at least one reliably identified peptide, the MS2 rescue module 820 is further configured to derive MS3 precursor masses in step 824 for a non-reliably identified peptide using an MS2 precursor mass for the potential crosslink and MS3 precursor masses for the reliably identified peptide, and to determine in step 826 if the corresponding MS2 spectra contain the derived MS3 precursor masses.

Responsive to an affirmative determination in step 826 that the corresponding MS2 spectra contain the derived MS3 precursor masses, the MS2 rescue module 820 in step 828 performs a PSM search utilizing the MS2 spectra and the derived MS3 precursor masses. A negative determination in step 826 illustratively terminates the current processing instance of the MS2 rescue module 820.

Performing the PSM search in step 828 illustratively comprises performing a first PSM search on a first MS2 spectrum using a first one of the derived precursor masses, and performing a second PSM search on a second MS2 spectrum using a second one of the derived precursor masses.

Responsive to the PSM search of step 828 yielding at least one PSM, further evaluation of the candidate peptide for the potential crosslink is performed using said at least one PSM. These one or more PSMs are referred to as "rescued PSMs" obtained by MS2 rescue module 820 in the present embodiment.

As mentioned previously, the MS2 rescue module 820 can be triggered under other conditions. For example, the MS2 rescue module can be triggered for a potential crosslink responsive to detection of corresponding MS3 spectra representing different charge states of a single candidate peptide.

The version of MaXLinker™ embodied in the process 800, like that of the process 400, implements a search algorithm to efficiently identify crosslinks using stringent validation filters arranged in a processing pipeline. In some embodiments, the MaXLinker™ workflow implements an MS2-MS3 approach that is configured to discard any crosslink candidate without sufficient information from the MS3 level. An example of this approach was previously described in conjunction with FIG. 3. The general experimental methodology for this MS2-MS3 approach involves precursor selection at multiple levels of mass spectrometry. First, ions above certain threshold charge state (typically +3 or +4) will be selected for fragmentation at the MS2 level to yield signature ions with a predefined mass difference ($\Delta m = 31.97$ for DSSO). Further, an iterative search is performed to select ion pairs with mass difference signature Δm to perform fragmentation at the MS3 level to yield two MS3 spectra per peptide in an ideal scenario, illustrated by Case 1 in the process 800 of FIG. 8. Other types of mass spectrometry approaches can be used in other embodiments.

The crosslink search in illustrative embodiments begins at the MS3 level by performing precursor-based mass validation, which facilitates the elimination of potential false positives. If a set of MS3 spectra representing a potential crosslink passes the precursor-based mass validation in step 808, it is verified through additional validation filters in step 814. For those cases that fail to pass the precursor-based mass validation in step 808, MaXLinker™ inspects the corresponding MS1 spectrum to verify misassignment of the monoisotopic precursor mass, considering the complexity of crosslink spectra due to their high precursor masses, and provides an adjustment to the precursor in step 810. Such cases are systematically examined and passed on to the next filter in step 814 if they satisfy the precursor-based mass validation in step 812 with the adjusted precursor mass.

The remaining candidate MS3 spectra are sent to the MS2 rescue module 820 if a peptide sequence for either of the peptides could reliably be identified from the MS3 spectra, illustrated by Case 2 in the process 800 of FIG. 8. Such MS3 spectra in this embodiment are also referred to as "informative MS3 spectra." Informative MS3 spectra are associated with what is more generally referred to herein as a "reliably identified peptide," while "uninformative MS3 spectra" are associated with what is more generally referred to herein as a "non-reliably identified peptide." Peptide A in Case 2 is an example of a reliably identified peptide, and Peptide B in Case 2 is an example of a non-reliably identified peptide. The reliability of the peptide identification in this embodiment is based on the informative or uninformative nature of the corresponding MS3 spectra of that peptide.

Accordingly, Case 2 has informative MS3 spectra for Peptide A and uninformative MS3 spectra for Peptide B. This is in contrast to Case 1 which has informative MS3 spectra for both Peptide A and Peptide B.

The MS2 rescue module 820 is illustratively triggered if the candidate spectra failed to pass the precursor-based mass validation of step 808 or step 812 and MS3 spectra for one of the two peptides failed to provide reliable PSM, as in Case 2. In this case, considering by way of example a scenario in which the mass spectrometry produces an incorrect pair of MS3 spectra having the mass difference signature Δm by chance, the MS2 rescue module 820 of this MaXLinker™ embodiment attempts to obtain sequence information for that peptide by utilizing fragment ions from the corresponding MS2 spectrum.

Figure 9B:
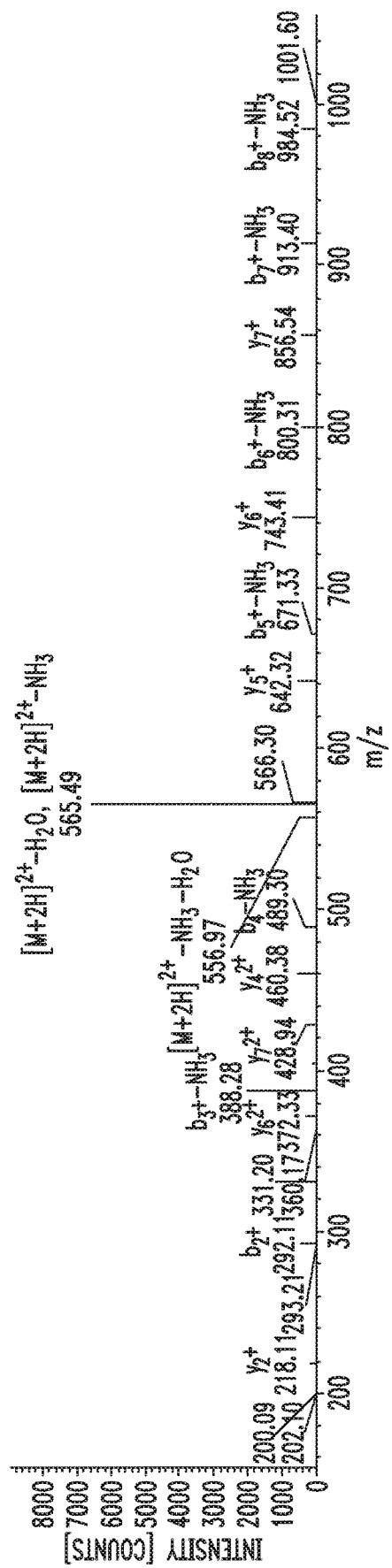
Figure 9C:
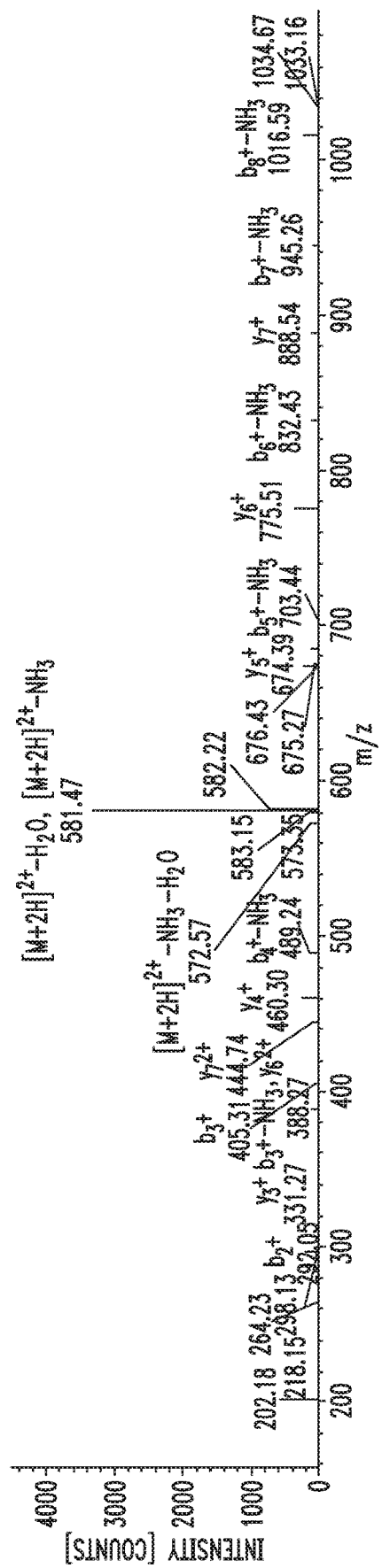
Figure 9D:
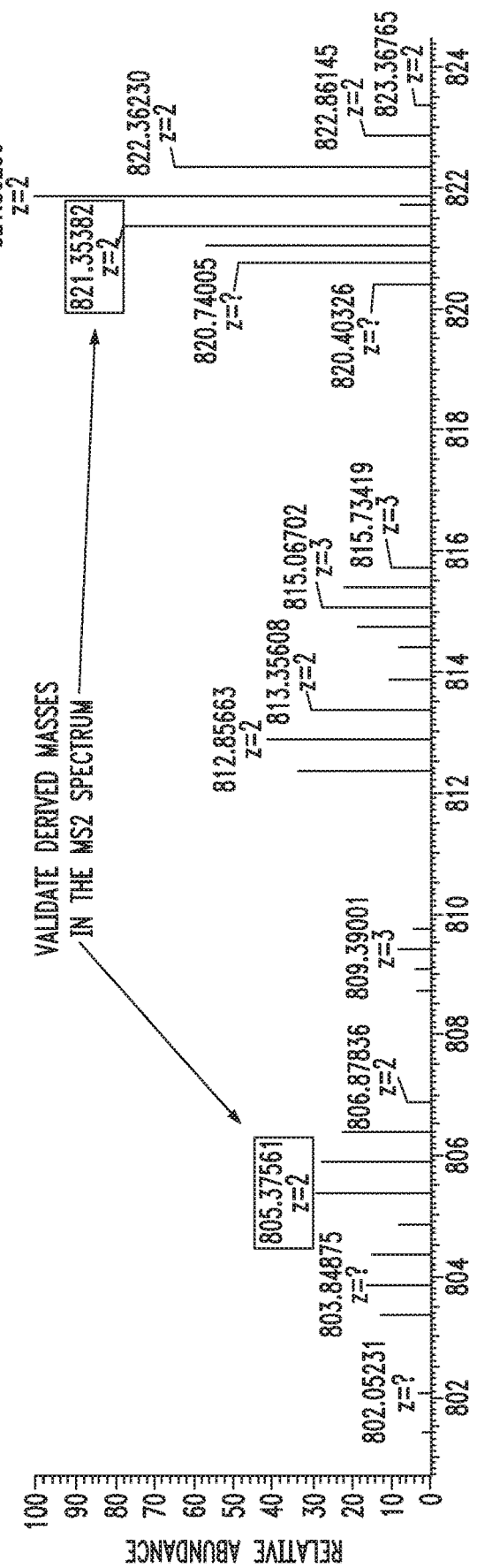
Figure 9E:
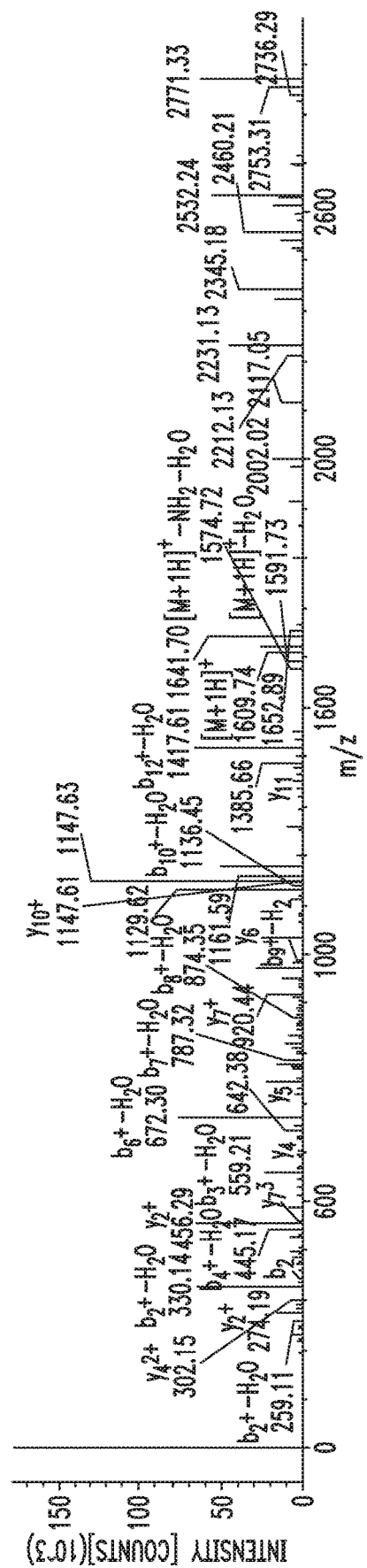
Figure 9F:
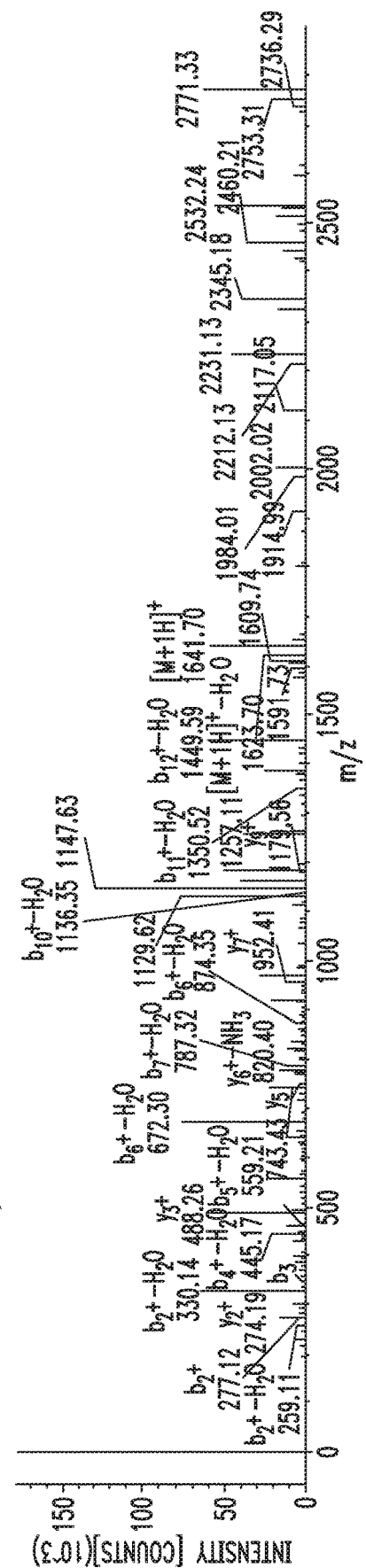

FIG. 9A shows an example of the operation of the MS2 rescue module 820 in this type of situation. After first determining in step 822 that at least one peptide has informative MS3 spectra, precursor masses for the peptide with uninformative MS3 spectra (Peptide B in Case 2) are derived in step 824 using the MS2 precursor mass and MS3 precursor masses of the other peptide that has informative MS3 spectra (Peptide A in Case 2). Such an arrangement accounts for both long and short DSSO modifications. Further, a validation search is performed on fragment ions of the corresponding MS2 spectrum in step 826 to confirm presence of the derived MS3 precursor masses. Subsequently, a PSM search is performed in step 828 on the deconvoluted MS2 spectrum once with each derived mass as the precursor mass. If the search in step 828 returns at least one reliable PSM, the candidate crosslink and the corresponding sequence information for the one or more "rescued" peptides are provided to step 814 for further validation processing of the type previously described. More detailed views of portions of the spectra and related data tables of the FIG. 9A example are shown in FIGS. 9B through 9F.

Additionally, the MS2 rescue module 820 in the present embodiment also accounts for cases in which the mass spectrometry produces two pairs of MS3 spectra with mass difference signature Δm, but both pairs represent different charge states of one of the two peptides.

Figure 10A:
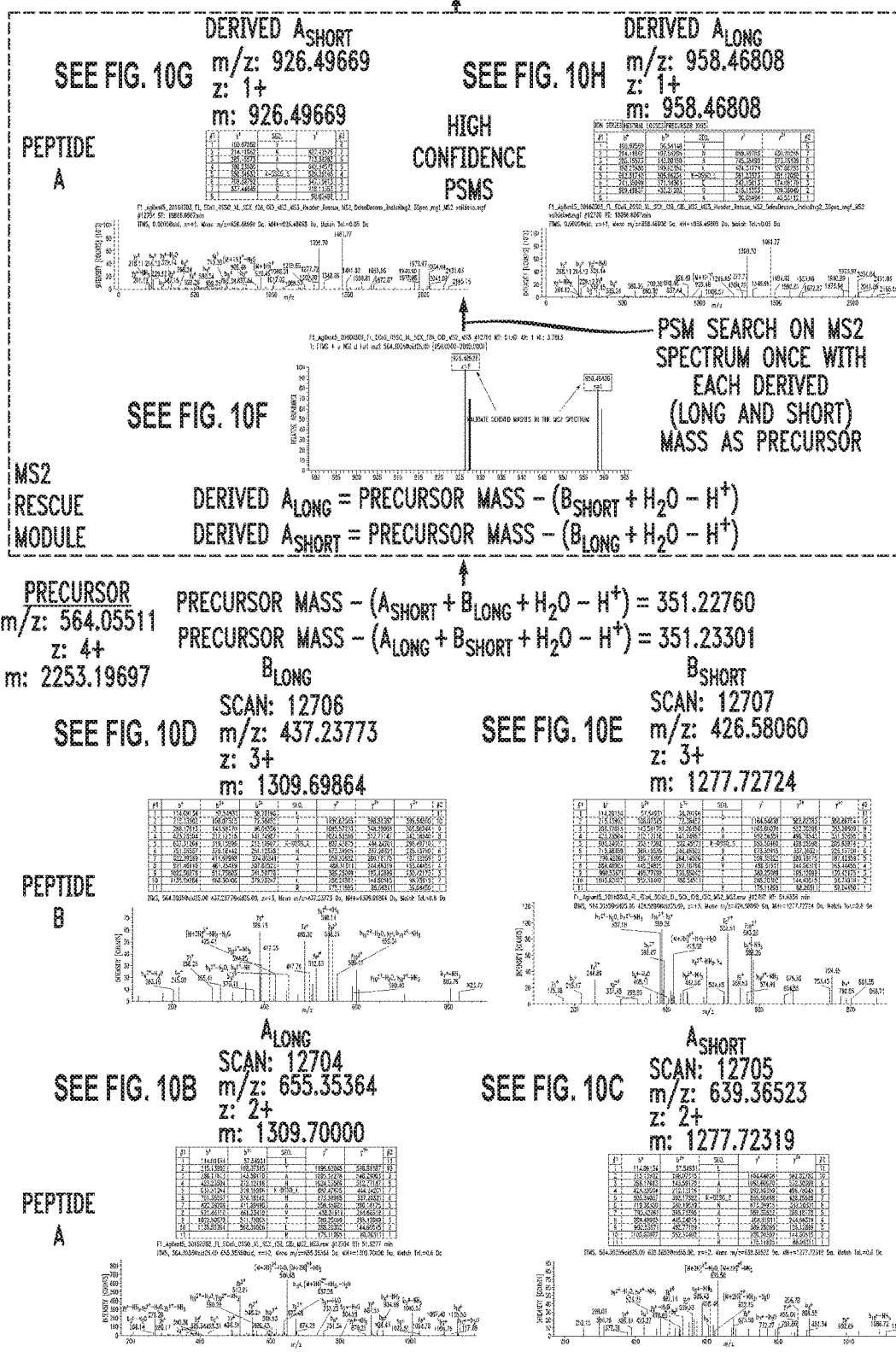
Figure 10B:
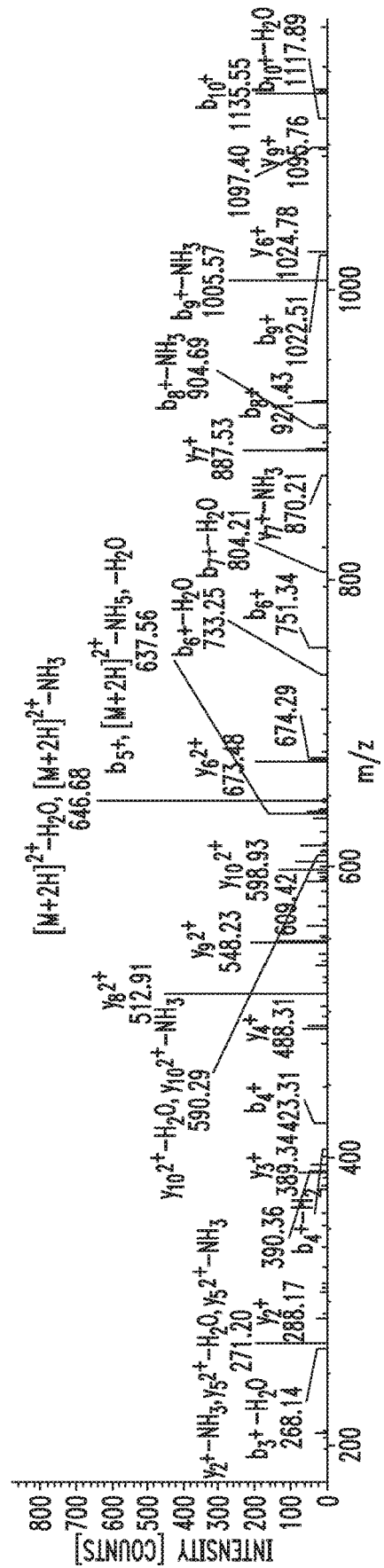
Figure 10C:
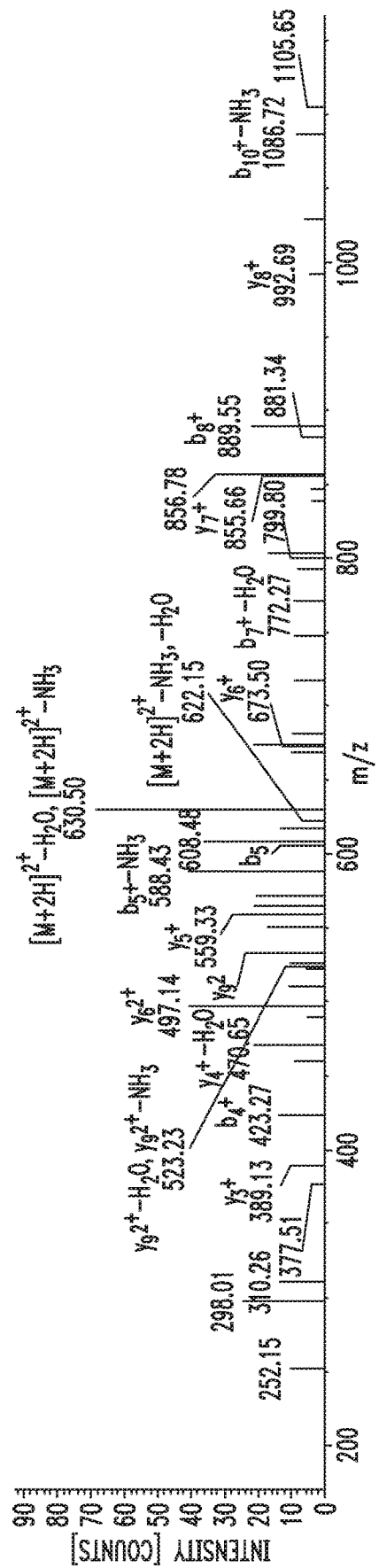
Figure 10D:
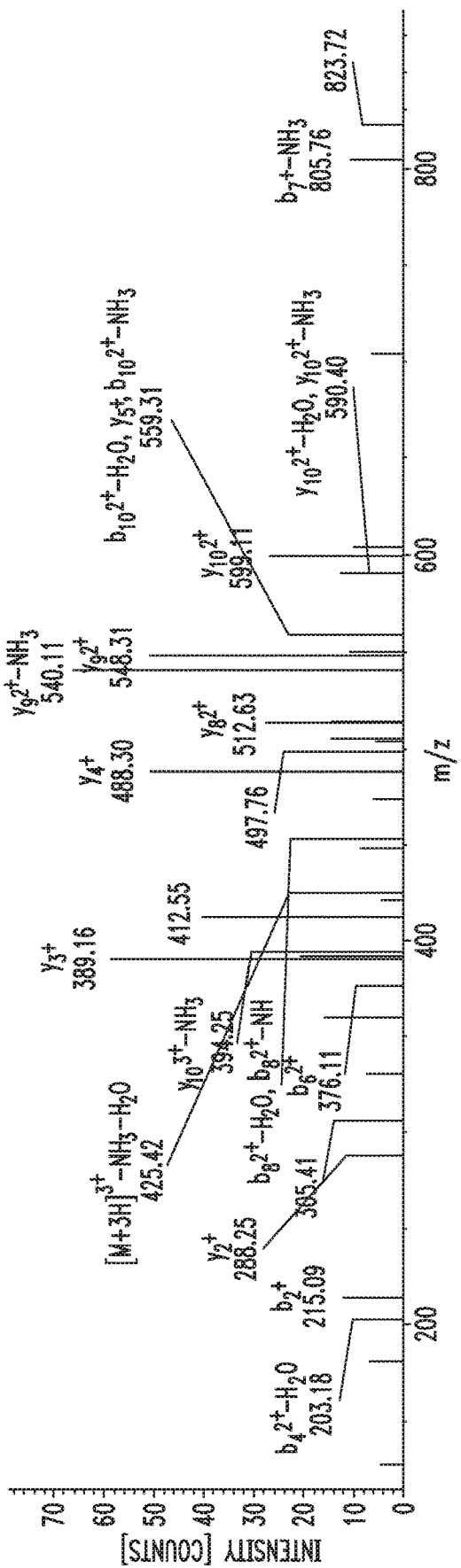
Figure 10E:
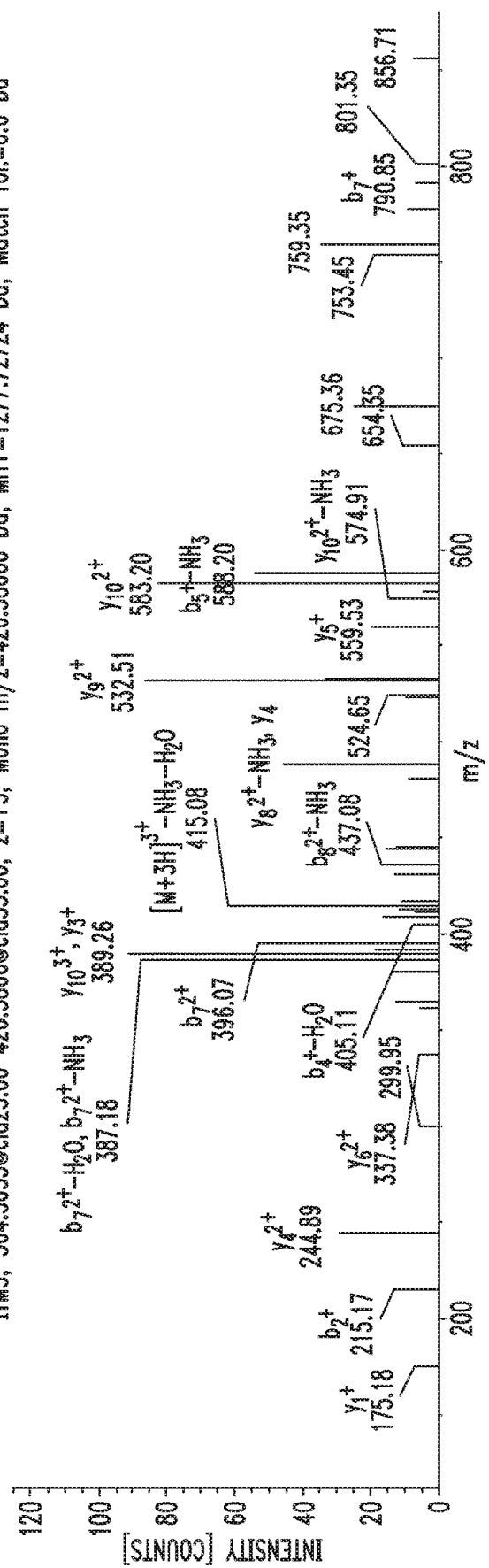
Figure 10F:
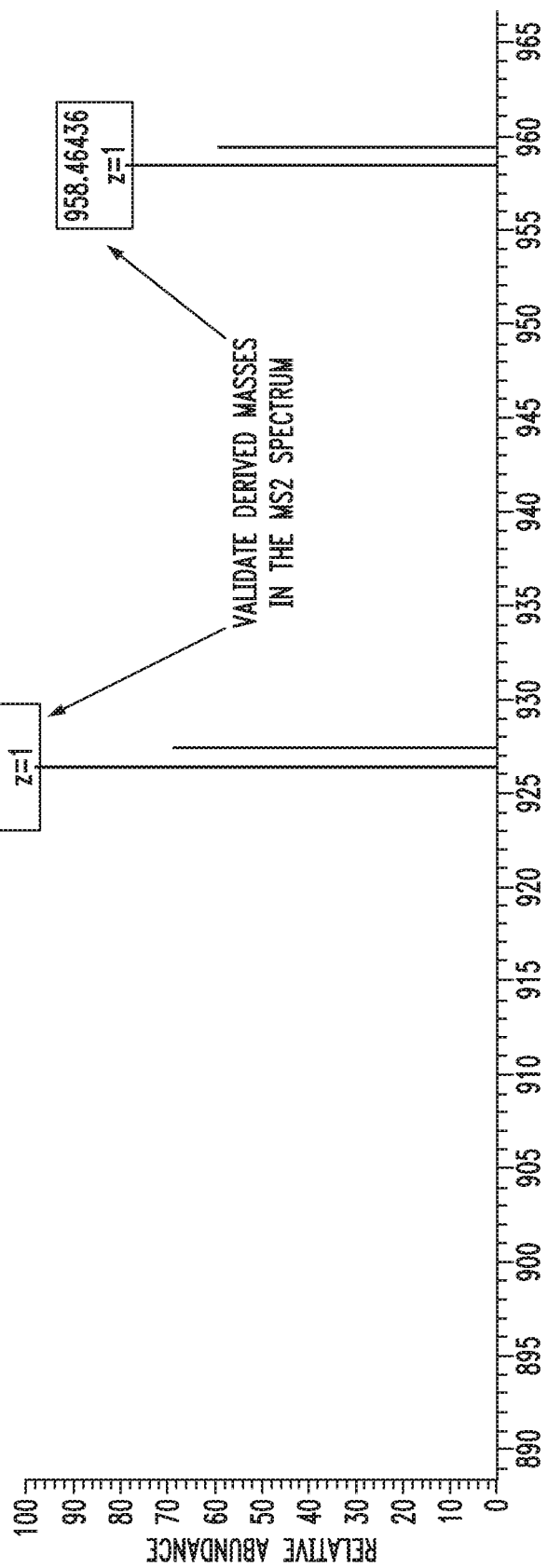
Figure 10G:
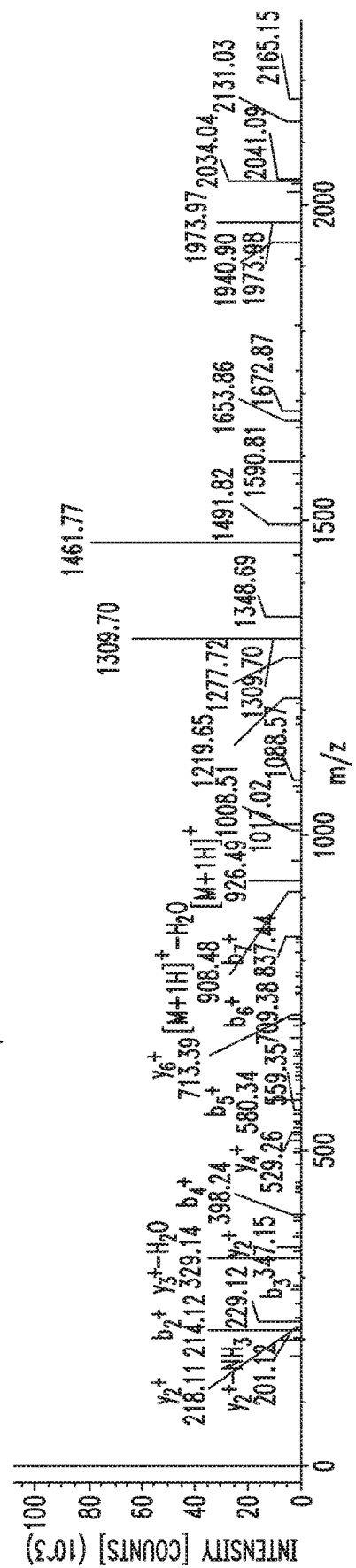
Figure 10H:
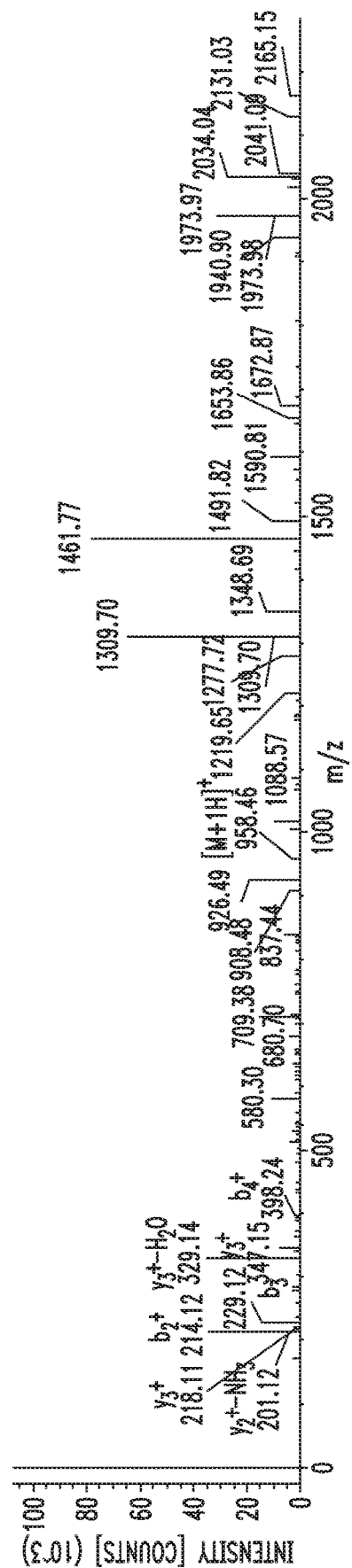

FIG. 10A shows an example of the operation of the MS2 rescue module 820 in this type of situation. More detailed views of portions of the spectra and related data tables of the FIG. 10A example are shown in FIGS. 10B through 10H.

It is to be appreciated that the examples of FIGS. 9A-9F and 10A-10H illustrate possible operating scenarios of MS2 rescue module 820 in illustrative embodiments. Other embodiments can implement additional or alternative processing operations in a given MS2 rescue module, and that term as used herein is therefore intended to be broadly construed.

Upon completion of the search, a list of unique identified crosslinks is obtained by merging redundant crosslink spectrum match (CSM) entries, with each such crosslink having a confidence score assigned thereto in the manner described elsewhere herein. Accordingly, in the case of multiple CSMs with different crosslink positions, only one of them was retained in the list.

Like the FIG. 4 process, the FIG. 8 process can be iterated by obtaining additional input data and repeating the steps described above. A target-decoy strategy is illustratively utilized to establish the FDR as per Equation (2) above, and precision of the identified crosslinks can be determined as per Equation (3) above.

Figure 7:
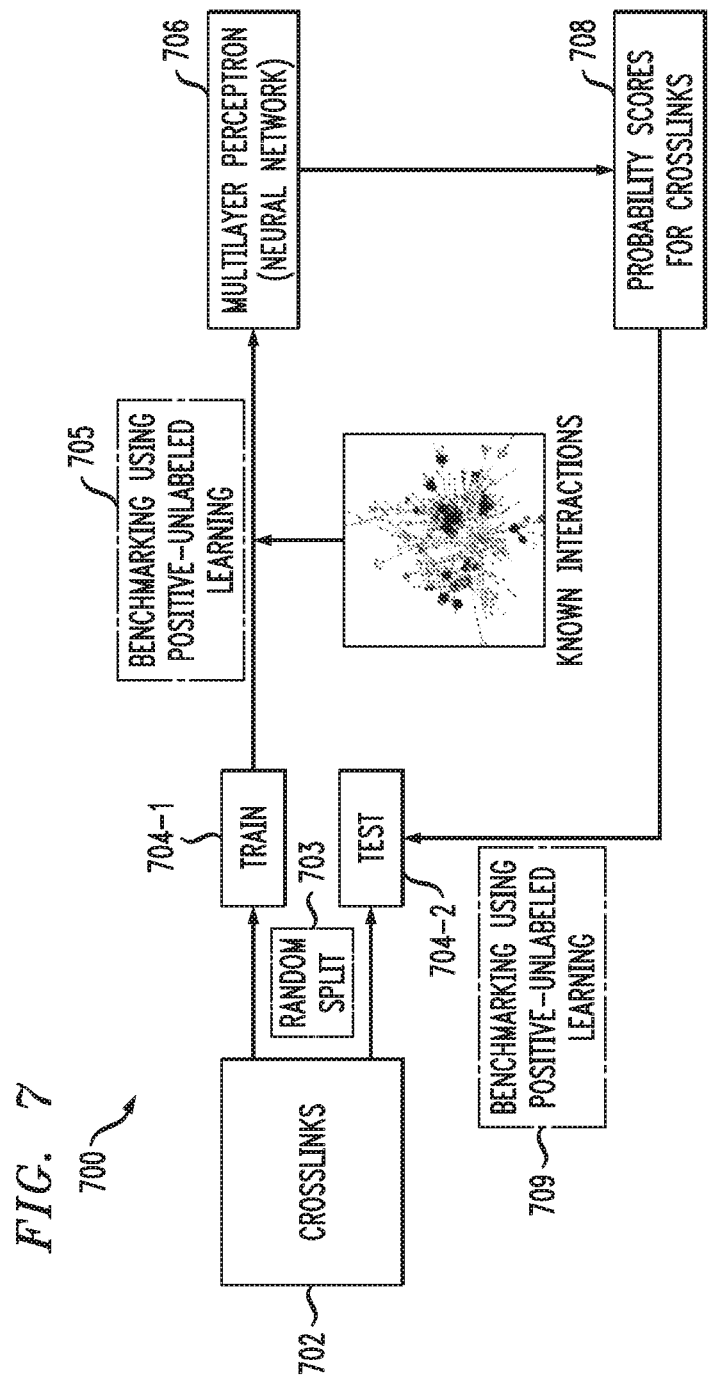
FIG. 7 shows machine learning based probability scoring functionality of the FIG. 1 system in an illustrative embodiment.

Machine learning based optimization of the type described in conjunction with FIG. 7 can be performed. For example, machine learning based optimization utilizing precision as a metric can provide significant additional advantages for accurate and efficient large-scale mapping of protein-protein interactions. As indicated above, precision as defined in Equation (3) represents the fraction of identified interprotein crosslinks that correspond to known protein-protein interactions.

Again, although DSSO is utilized by way of example as an MS-cleavable crosslinker in certain MaXLinker™ embodiments disclosed herein, other embodiments can utilize any of a wide variety of other types of MS-cleavable crosslinkers, and the illustrative embodiments are not limited in this regard.

The particular process steps illustrated in the FIG. 8 embodiment are also presented by way of illustrative example only, and additional or alternative process steps can be used in other embodiments. For example, different arrangements of header matching and mass validation filters can be used. Additionally or alternatively, different arrangements of the MS2 rescue module 820 can be used.

Figure 11A:
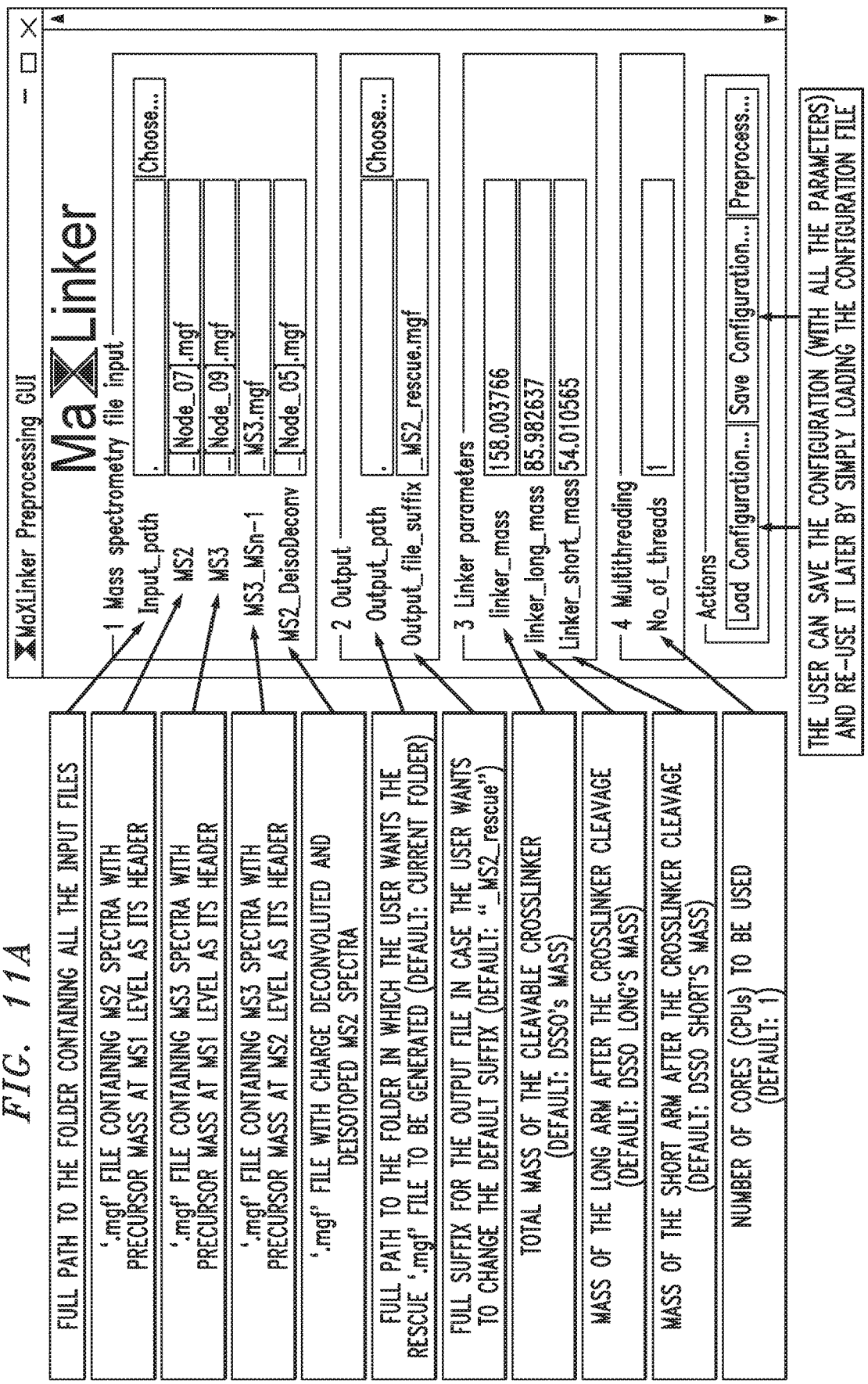
FIGS. 11A through 11I show portions of example user interfaces for a crosslink identification and validation algorithm in an illustrative embodiment.
Figure 11B:
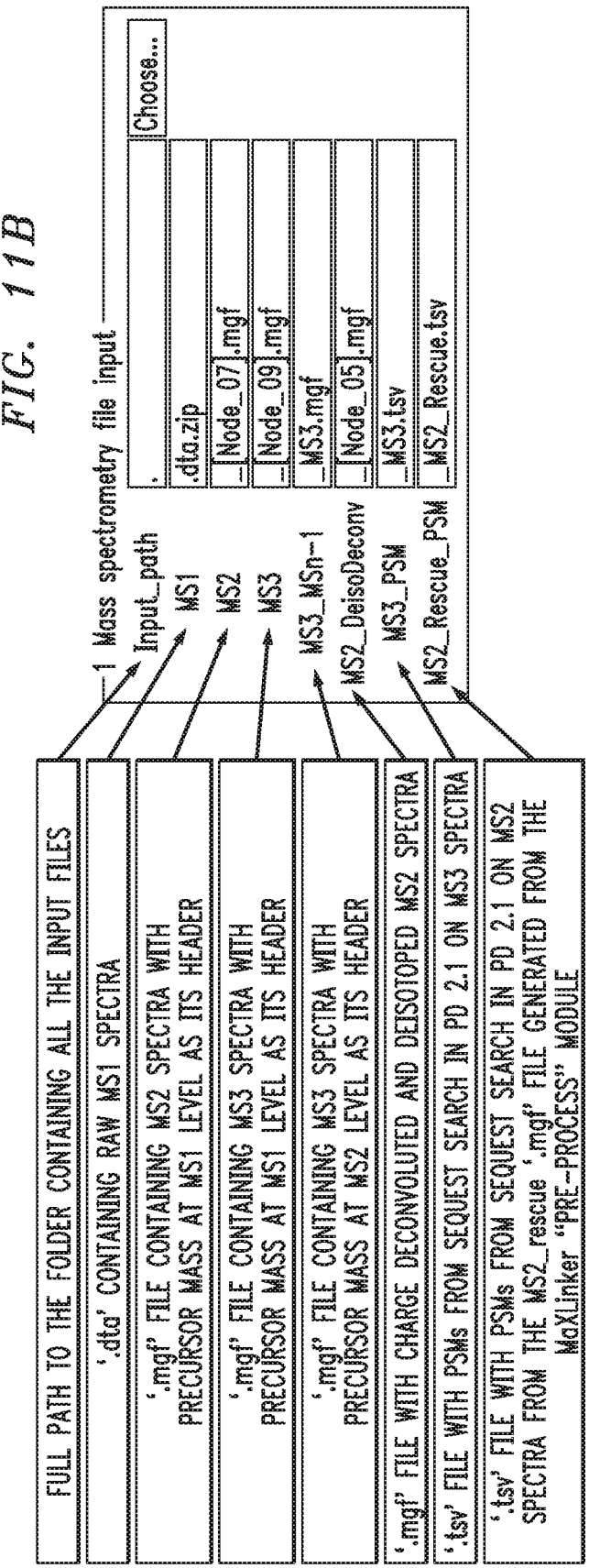
Figure 11C:
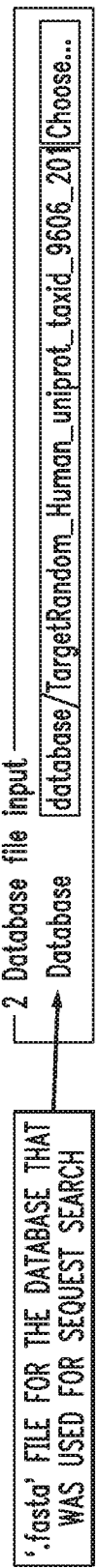
Figure 11D:
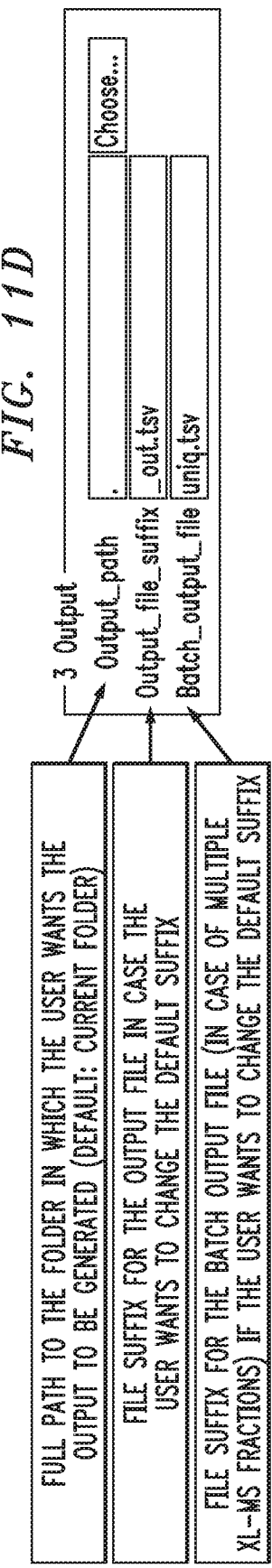
Figure 11E:
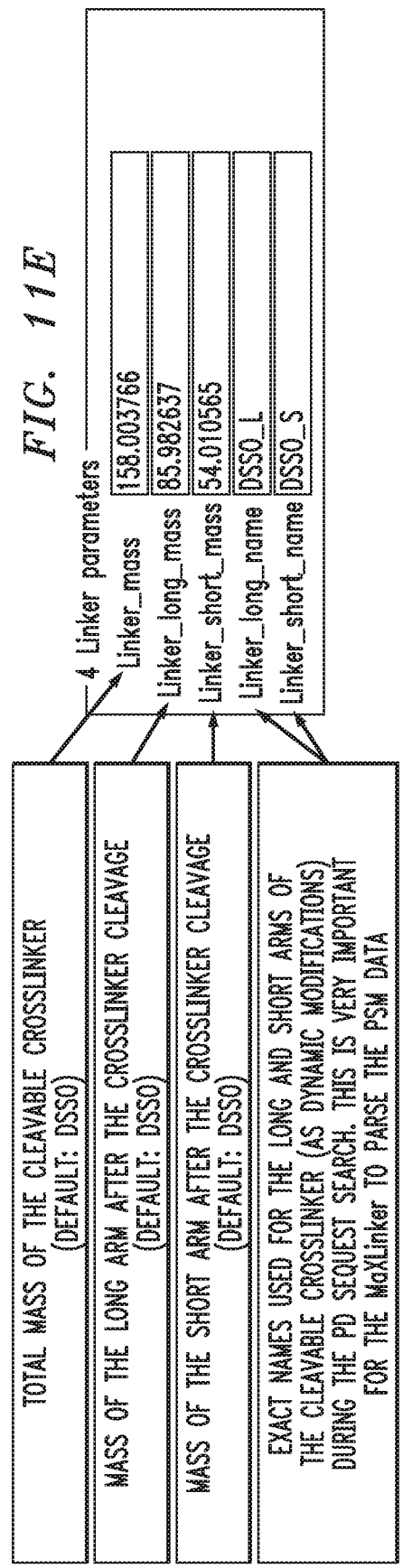
Figure 11F:
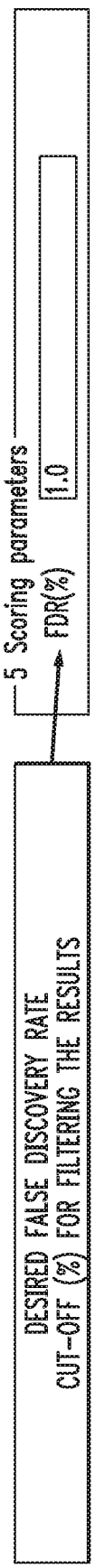
Figure 11G:
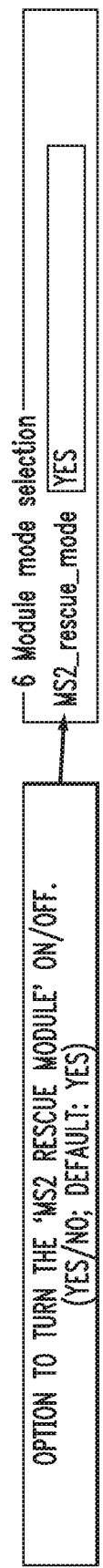
Figure 11H:
Figure 11I:

Portions of example user interfaces for an illustrative embodiment of MaXLinker™ are shown in FIGS. 11A through 11I. In FIG. 11A, a screen shot of an example user interface is shown, comprising groups of search configuration entry elements denoted by numerals 1, 2, 3 and 4, and an actions bar at the lower portion of the screenshot. FIGS. 11B through 11H show other examples of groups of search configuration entry elements, denoted by respective numerals 1 through 7. FIG. 11I shows another view of an actions bar. A wide variety of other user interface arrangements can be used in other embodiments.

Figure 12:
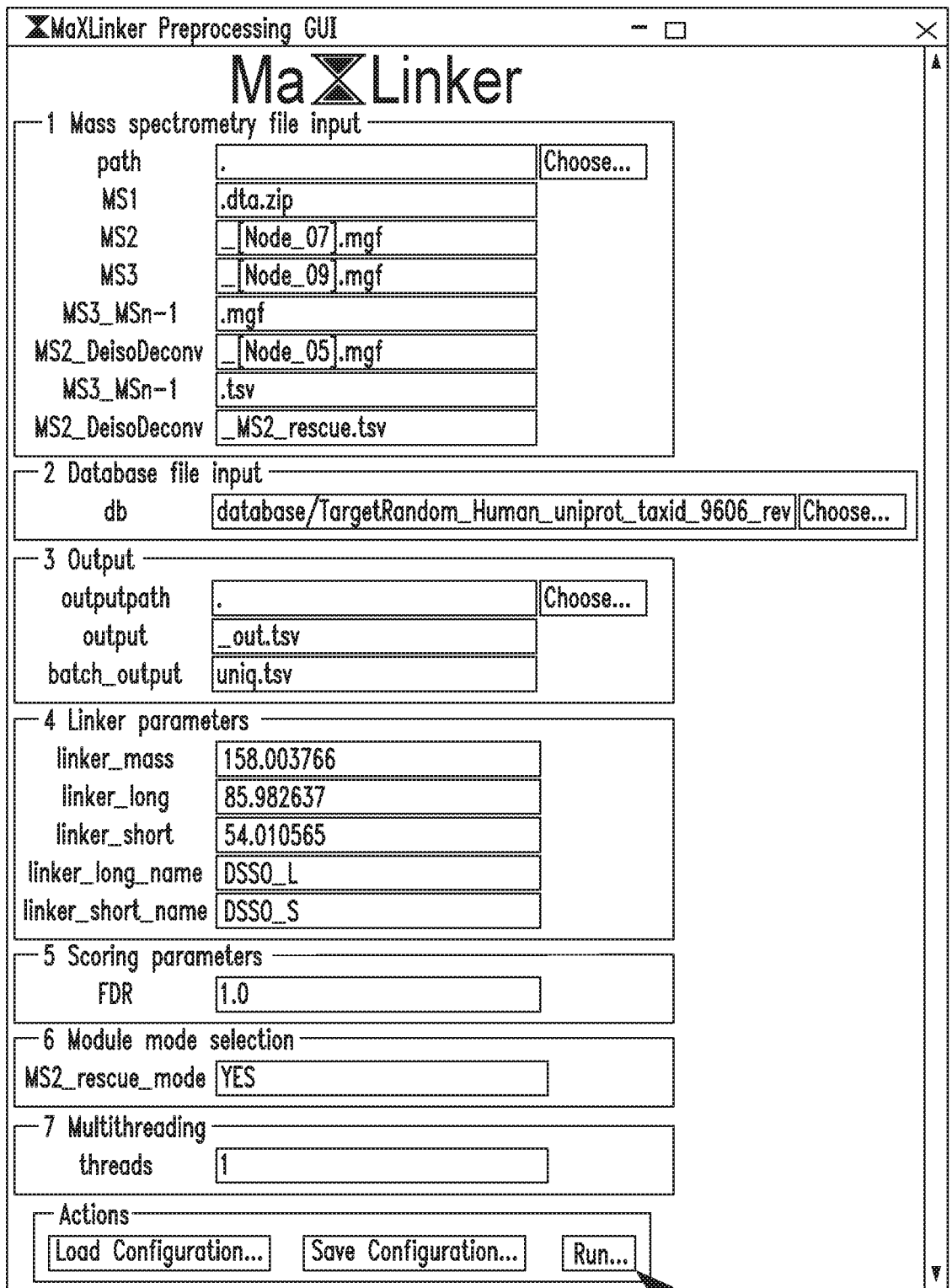
FIG. 12 shows additional portions of a user interface illustrating a search workflow for a crosslink identification and validation algorithm.
Figure 12:
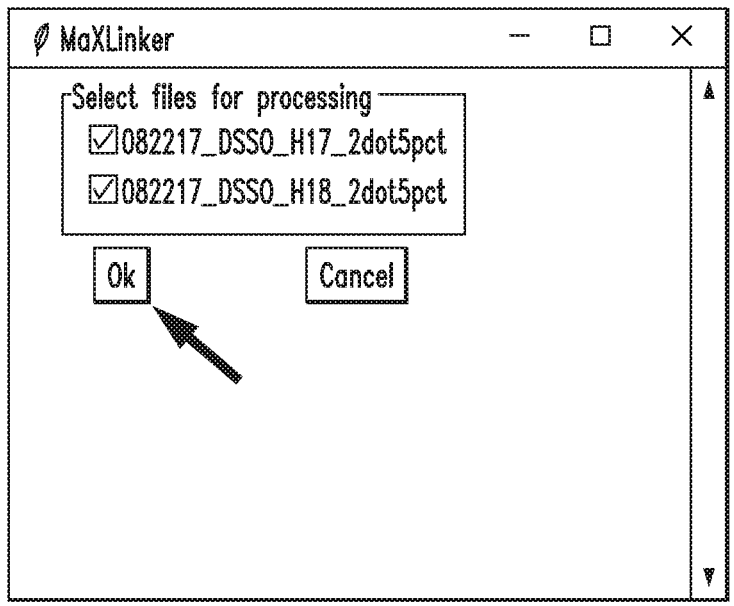
Figure 12:
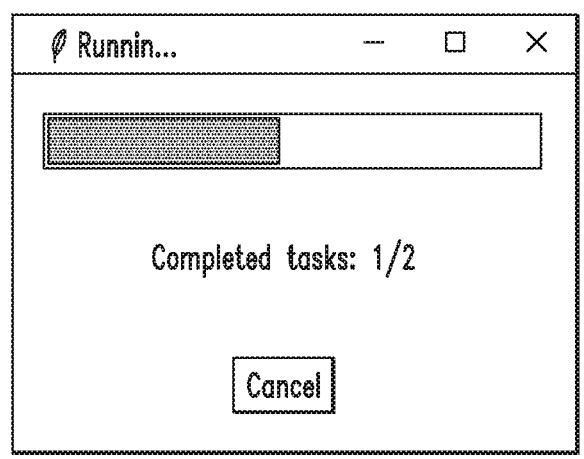
Figure 12:
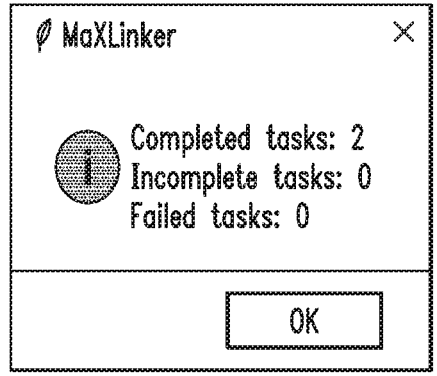

FIG. 12 shows an example search workflow performed by MaXLinker™ in an illustrative embodiment, with a user interface comprising search configuration entry elements of the type illustrated in FIGS. 11A through 11I. In this example, the user actuates a Run icon on the action bar, after populating the configuration entry elements for the search, and subsequently selects files for processing. Status information regarding the search is provided to the user as the search workflow progresses. This particular workflow is only an example, and numerous other search workflows can be instantiated in other embodiments.

The performance advantages of the MaXLinker™ embodiment of FIG. 8 have been demonstrated using a number of different evaluations, which will now be described in further detail.

One such evaluation involved utilizing MS2-MS3 XLMS raw files for six E. coli fractions from the above-cited Liu et al. reference.

In this evaluation, we first performed crosslink search using MaXLinker™ at 1% FDR. We noted that the fraction of non-E. coli CSMs was less than 1%, and for the majority of the identifications, the peptide sequence information was derived from MS3 spectra.

Next, we compared the results with crosslinks identified using XlinkX v2.0 at 1% FDR on the same set of raw files. Our analysis showed that MaXLinker™ clearly outperforms XlinkX v2.0, as indicated by a highly significant difference in the fraction of misidentifications (non-E. coli CSMs).

We then examined the overlap between identifications from MaXLinker™ and XlinkX v2.0. It was found that the overlapping fraction from XlinkX v2.0 has only 0.6% misidentifications, whereas the non-overlapping fraction has an astounding 33.1% misidentifications. Further, using precision as a quality metric, we observed similar results. When we repeated the quality analyses by filtering crosslinks from XlinkX v2.0 at different "Δ XlinkX score" cutoffs, we observed that MaXLinker™ consistently finds 13-31% more crosslinks than XlinkX v2.0 at comparable quality.

Importantly, the CSMs identified exclusively by MaXLinker™ are of three-fold higher quality than the exclusive identifications by XlinkX v2.0, even at the highly stringent cutoff of Δ XlinkX score ≥50. These results clearly demonstrate that MaXLinker™ outperforms XlinkX v2.0 for CSM identifications in both specificity and sensitivity.

In another evaluation, we crosslinked commercially available Bovine Glutamate Dehydrogenase 1 protein (GLUD1) using DSSO and configured a CID-MS2-HCD-MS3 experiment using the MaXLinker™ embodiment of FIG. 8 to perform two individual CSM searches, as follows:

Search 1: using Bovine GLUD1 sequence as the search database, yielding 43 crosslinks; and Search 2: using a concatenated database with Bovine GLUD1 and a full proteome of S. cerevisiae, yielding 37 crosslinks.

We then examined the overlap between crosslinks from Search 1 and Search 2 to inspect MaXLinker™'s ability to find true crosslinks from a single protein in a false search space. We observed that 34 of 37 (92%) crosslinks from Search 2 were overlapping with the ones from Search 1. Out of the remaining three crosslinks, two have one of the peptides in the pair from S. cerevisiae proteome (false search space). Interestingly, 9 crosslinks were identified exclusively in Search 1. Upon close examination, we noted that MaXLinker™ rejected those crosslink candidates due to either (i) its stringent validation filters or (ii) lower confidence in their PSM assignments, attributable to the drastic increase in the number of competing candidate peptides for individual spectra.

On the other hand, when we performed similar analysis using XlinkX v2.0, Search 1 and Search 2 yielded 35 and 140 crosslinks, respectively. Out of the 140 crosslinks from Search 2, 30 were overlapping with Search 1 and the remaining 110 had at least one of the peptides from S. cerevisiae proteins. For further validation of the identified crosslinks, we mapped crosslinks from Search 1 onto a three-dimensional structure of Bovine GLUD1. We observed that 14 of the 17 mapped crosslinks were within the theoretical distance constraint (30 Å), and the remaining three crosslinks were within 39 Å, validating reliable quality of our identifications. Again, this particular evaluation clearly demonstrated the superior performance of MaXLinker™ in XLMS relative to the conventional XlinkX v2.0 approach.

In a further evaluation, we performed proteome-wide XLMS on K562 cell lysate. Employing the MaXLinker™ embodiment of FIG. 8, we identified 9,319 and 12,436 unique crosslinks at 1% and 2% FDR, respectively. Furthermore, we validated the quality of crosslinks using available three-dimensional structure.

For the K562 cell lysate evaluation, we again configured a CID-MS2-HCD-MS3 experiment using the MaXLinker™ embodiment of FIG. 8. We utilized strong cation exchange chromatography (SCX) for pre-fractionation of crosslinked proteome samples, as well as hydrophilic interaction chromatography (HILIC), in order to capture the most comprehensive set of crosslinks.

We then employed MaXLinker™ for crosslink identification, yielding 9,319 crosslinks (8,051 intraprotein and 1,268 interprotein with precision 74.2%) at 1% FDR. To validate the identified crosslinks utilizing available three-dimensional structures, we mapped crosslinks from a large biological complex 26S proteasome on to its structure. Out of the 100 crosslinks mapped to structure, 90 were within the theoretical constraint of 30 Å. Additionally, we could validate one crosslink that was exceeding 30 Å, utilizing a different structure, suggesting potential conformational changes in the corresponding subunits. Six out of the remaining nine crosslinks were within 35 Å, and all the others were within 50 Å, demonstrating the high quality of the crosslink identifications. Additionally, interprotein crosslinks identified at 1% FDR represent 160 unambiguous novel interactions. Furthermore, in order to validate those novel interactions using an orthogonal experimental methodology, a subset of were randomly picked and tested using a Protein Complementation Assay (PCA). The fraction of detected interactions revealed by XLMS were statistically indistinguishable (p=0.325) from the positive reference set of well-established interactions previously reported but significantly different ($p=1.8 \times 10^{-5}$) from a negative reference set containing randomized protein pairs.

These evaluation results demonstrate the high quality of the crosslinks identified by illustrative embodiments of MaXLinker™. Moreover, such embodiments can efficiently eliminate false positives with minimum number of false negatives.

Substantial performance advantages are therefore provided in illustrative embodiments relative to conventional approaches such as XlinkX v2.0. For example, our analyses demonstrate that a significant fraction of the crosslinks identified by XlinkX v2.0 rely completely on MS2 spectra with no sequence information from corresponding MS3 spectra at all. Furthermore, our analyses reveal that a majority of the misidentifications produced by XlinkX v2.0 were identified using MS2 spectrum alone. Unlike such conventional approaches, MaXLinker™ embodiments disclosed herein illustratively initiate searching from the MS3 level and reject any potential crosslink if it lacks adequate MS3 information for at least one of the peptides. This fundamental difference in algorithmic design provides MaXLinker™ in illustrative embodiments with an enhanced ability to eliminate false positives without compromising on the number of crosslink identifications.

Additional details regarding materials and methods utilized in these evaluations can be found in the attached Appendix. Such materials and methods are examples only, and should not be considered limiting in any way.

As indicated previously, illustrative embodiments can provide significant advantages over conventional approaches such as the above-noted XlinkX v2.0, including high precision and reduced FDR.

In addition, crosslink identification and validation algorithms such as MaXLinker™ in illustrative embodiments are highly flexible, in that they are easily portable across multiple processing platforms and associated operating systems, in some cases exhibiting minimal hardware and computational requirements.

Furthermore, MaXLinker™ and other crosslink identification and validation algorithms disclosed herein can be adapted for use with other types of crosslinkers, including MS-cleavable crosslinkers other than DSSO.

Illustrative embodiments such as MaXLinker™ outperform other available methods such as XlinkX v2.0 in terms of both quality and quantity of true crosslinks identified.

The MaXLinker™ embodiments disclosed herein facilitate the efficient identification of protein-protein interactions. Such interactions play a vital role in nearly all cellular functions. Hence, understanding their interaction patterns and associated three-dimensional structural conformations utilizing the techniques disclosed herein can provide crucial insights about the underlying molecular mechanisms for a wide variety of disease phenotypes and in numerous other crosslink processing contexts.

Some embodiments implement machine learning functionality that can further reduce the number of false positives. The machine learning functionality in illustrative embodiments provides strict quality control in identification and validation of crosslinks, facilitating the detection of protein-protein interactions with high quality and reliability.

It is to be understood that the various embodiments disclosed herein are presented by way of illustrative example only, and should not be construed as limiting in any way. Numerous alternative arrangements for crosslink identification and validation can be utilized in other embodiments. For example, references herein to an embodiment of MaXLinker™ having particular features should not be viewed as a requirement that other embodiments of MaXLinker™ necessarily include those particular features.

Accordingly, those skilled in the art will readily appreciate that a wide variety of distinct MaXLinker™ embodiments as well as numerous other alternative embodiments can be implemented using the disclosed teachings.

For example, those skilled in the art will recognize that alternative processing operations and associated system entity configurations can be used in other embodiments. It is therefore possible that other embodiments may include additional or alternative system elements, relative to the elements of the illustrative embodiments. Also, the particular processing modules, crosslink identification and validation algorithms, machine learning systems and other aspects of the illustrative embodiments can be varied in other embodiments.

It should also be noted that the above-described information processing system arrangements are exemplary only, and alternative system arrangements can be used in other embodiments.

A given client, server, processor or other component in an information processing system as described herein is illustratively configured utilizing a corresponding processing device comprising a processor coupled to a memory. The processor executes software program code stored in the memory in order to control the performance of processing operations and other functionality. The processing device also comprises a network interface that supports communication over one or more networks.

The processor may comprise, for example, a microprocessor, an ASIC, an FPGA, a CPU, an ALU, a DSP, a GPU or other similar processing device component, as well as other types and arrangements of processing circuitry, in any combination. For example, one or more modules or other components of crosslink processing platform 102 as disclosed herein can be implemented using such circuitry.

The memory stores software program code for execution by the processor in implementing portions of the functionality of the processing device. A given such memory that stores such program code for execution by a corresponding processor is an example of what is more generally referred to herein as a processor-readable storage medium having program code embodied therein, and may comprise, for example, electronic memory such as SRAM, DRAM or other types of random access memory, flash memory, ROM, magnetic memory, optical memory, or other types of storage devices in any combination.

Articles of manufacture comprising such processor-readable storage media are considered embodiments of the invention. The term "article of manufacture" as used herein should be understood to exclude transitory, propagating signals.

Other types of computer program products comprising processor-readable storage media can be implemented in other embodiments.

In addition, embodiments of the invention may be implemented in the form of integrated circuits comprising processing circuitry configured to implement processing operations associated with crosslink identification and machine learning as well as other related functionality.

Processing devices in a given embodiment can include, for example, computers, servers and/or other types of devices each comprising at least one processor coupled to a memory, in any combination. For example, one or more computers, servers, storage devices or other processing devices can be configured to implement at least portions of a crosslink processing platform comprising a crosslink identification and validation algorithm and/or a machine learning system as disclosed herein. Communications between the various elements of an information processing system comprising processing devices associated with respective system entities may take place over one or more networks.

An information processing system as disclosed herein may be implemented using one or more processing platforms, or portions thereof.

For example, one illustrative embodiment of a processing platform that may be used to implement at least a portion of an information processing system comprises cloud infrastructure including virtual machines implemented using a hypervisor that runs on physical infrastructure. Such virtual machines may comprise respective processing devices that communicate with one another over one or more networks.

The cloud infrastructure in such an embodiment may further comprise one or more sets of applications running on respective ones of the virtual machines under the control of the hypervisor. It is also possible to use multiple hypervisors each providing a set of virtual machines using at least one underlying physical machine. Different sets of virtual machines provided by one or more hypervisors may be utilized in configuring multiple instances of various components of the information processing system.

Another illustrative embodiment of a processing platform that may be used to implement at least a portion of an information processing system as disclosed herein comprises a plurality of processing devices which communicate with one another over at least one network. Each processing device of the processing platform is assumed to comprise a processor coupled to a memory.

Again, these particular processing platforms are presented by way of example only, and an information processing system may include additional or alternative processing platforms, as well as numerous distinct processing platforms in any combination, with each such platform comprising one or more computers, servers, storage devices or other processing devices.

For example, other processing platforms used to implement embodiments of the invention can comprise different types of virtualization infrastructure in place of or in addition to virtualization infrastructure comprising virtual machines. Thus, it is possible in some embodiments that system components can run at least in part in cloud infrastructure or other types of virtualization infrastructure.

It should therefore be understood that in other embodiments different arrangements of additional or alternative elements may be used. At least a subset of these elements may be collectively implemented on a common processing platform, or each such element may be implemented on a separate processing platform.

Also, numerous other arrangements of computers, servers, storage devices or other components are possible in an information processing system. Such components can communicate with other elements of the information processing system over any type of network or other communication media.

As indicated previously, components of the system as disclosed herein can be implemented at least in part in the form of one or more software programs stored in memory and executed by a processor of a processing device. For example, certain functionality associated with crosslink identification and validation algorithm and/or machine learning system components of a processing platform can be implemented at least in part in the form of software.

The particular configurations of information processing systems described herein are exemplary only, and a given such system in other embodiments may include other elements in addition to or in place of those specifically shown, including one or more elements of a type commonly found in a conventional implementation of such a system.

For example, in some embodiments, an information processing system may be configured to utilize the disclosed techniques to provide additional or alternative functionality in other contexts.

It is also to be appreciated that the particular process steps used in the embodiments described above are exemplary only, and other embodiments can utilize different types and arrangements of processing operations. For example, certain process steps shown as being performed serially in the illustrative embodiments can in other embodiments be performed at least in part in parallel with one another. Also, the ordering of the process steps can be varied in other embodiments.

It should again be emphasized that the embodiments of the invention as described herein are intended to be illustrative only. Other embodiments of the invention can be implemented utilizing a wide variety of different types and arrangements of information processing systems, processing platforms, processing modules, processing devices, processing operations, crosslinkers, crosslink identification and validation algorithms and machine learning systems than those utilized in the particular illustrative embodiments described herein. In addition, the particular assumptions made herein in the context of describing certain embodiments need not apply in other embodiments. These and numerous other alternative embodiments will be readily apparent to those skilled in the art.

APPENDIX

The following are additional details regarding materials and methods utilized in evaluation of illustrative embodiments described herein. Such details are considered as illustrative examples only and should not be construed as limiting in any way.

Cell Culture and Whole Cell Lysate Preparation

The K562 cells (ATCC® CCL-243™) were purchased from American Type Culture Collection (ATCC). The cells were maintained in the Iscove's Modified Dulbecco's Medium (IMDM) supplemented with 10% fetal bovine serum (FBS) at 37° C. with humidified ambient atmosphere containing 5% $CO_2$. The K562 cells were collected and washed three times with cold PBS. The cells were then resuspended in cold buffer composed of 50 mM HEPES, 150 mM NaCl, pH 7.5 supplemented with Protease Inhibitor Cocktail (Roche). The resuspended cells were lysed on ice by sonication (Amplitude 10% for 5 sec and repeat 6 times), followed by centrifugation at 15,000 g for 10 min at 4° C. The supernatant was collected and measured the protein concentration using Bio-Rad Protein Assay Dye (Bio-Rad).

Crosslinking of Bovine Glutamate Dehydrogenase (GDH) and Human Proteome

DSSO (Thermo Fisher Scientific) was freshly prepared as a 50 mM stock solution by dissolving in anhydrous DMSO. The 1 mg/mL pure bovine glutamate dehydrogenase (GDH) protein (Sigma) was reacted with 1 mM DSSO in 50 mM HEPES buffer, 150 mM NaCl, pH 7.5 for 30 min at room temperature. Similarly, the 1 mg/mL lysate of K562 cells were incubated with 1 mM DSSO for 1 hour at room temperature. Both crosslinking reactions were terminated by 50 mM Tris-Cl buffer, pH 7.5.

Processing of DSSO-Crosslinked Samples for Analysis

The DSSO-treated protein samples were processed as previously described. Briefly, the crosslinked GDH was denatured in 1% SDS, reduced by DTT, and alkylated with iodoacetamide, followed by precipitated in cold acetone-ethanol solution (acetone:ethanol:acetic acid=50:49.9:0.1, v/v/v). The precipitates were dissolved in 50 mM Tris-Cl, 150 mM NaCl, 2 M urea, pH 8.0 and digested by Trypsin Gold (Promega) at 37° C. overnight. After digestion, the sample was acidified by 2% trifluoroacetic acid-formic acid solution, desalted through Sep-Pak C18 cartridge (Waters), and dried using SpeedVac™ Concentrator (Thermo Fisher Scientific). The sample was then reconstituted in 0.1% trifluoroacetic acid and stored in −80° C. before mass spectrometry analysis. The DSSO-crosslinked human proteome was processed identically as described above except that the TPCK-treated trypsin was used for digestion and the sample was dissolved in a solution of 70% acetonitrile and 1% formic acid for further HILIC fractionation after dried.

Fractionation of Crosslinked Peptides by Hydrophilic Interaction Liquid Chromatography (HILIC)

The DSSO-crosslinked human peptides in 70% acetonitrile and 1% formic acid were fractionated and enriched by hydrophilic interaction liquid chromatography (HILIC). The HILIC fractionation was performed on a Dionex UltiMate 3000 Series instrument (Thermo Fisher Scientific) equipped with a TSKgel Amide-80 column (3 µm, 4.6 mm×15 cm; Tosoh). The three following solvents were used: 90% acetonitrile (solvent A), 80% acetonitrile and 0.005% trifluoroacetic acid (solvent B), 0.025% trifluoroacetic acid (solvent C). All the runs were performed at a flow rate of 600 µl/min using the following gradients: 0-5 min (0-98% B and 0-2% C); 5-55 min (98-75% B and 2-25% C); and 55-60 min (75-5% B and 25-95% C). The fractions were collected per 30 seconds. Each of the fractions were dried and stored at −80° C. for further analysis.

LC-MS$^n$ Analysis

The HILIC fractions were reconstituted in 0.1% trifluoroacetic acid. The samples were analyzed using an EASY-nLC 1200 system (Thermo Fisher Scientific) equipped with an 125-µm×25-cm capillary column in-house packed with 3-µm C18 resin (Michrom BioResources) and coupled online to an Orbitrap Fusion Lumos Tribrid mass spectrometer (Thermo Fisher Scientific). The LC analysis were performed using the linear gradients of solvent A composed of 0.1% formic acid and solvent B composed of 80% acetonitrile and 0.1% formic acid with a total run time of 180 min at a flow rate of 300 nl/min. For MS$^n$ data acquisition, the CID-MS2-HCD-MS3 method was used. Briefly, the MS precursors were detected in Orbitrap mass analyzer (375-1500 m/z, resolution of 60,000). The precursor ions with the charge of 4+ to 8+ were selected for MS analysis in Orbitrap mass analyzer (resolution of 30,000) with the collision energy of collision-induced dissociation (CID) at 25%. The peaks with a mass difference of 31.9721 Da, which is a signature of cleaved DSSO-crosslinked peptides, in CID-MS2 spectra were selected for further MS analysis. The selected ions were fragmented in IonTrap using higher-energy collisional dissociation (HCD) with the collision energy at 35%.

Validation of Newly Identified Protein Protein Interactions by Protein Complementation Assay (PCA)

The ORFs of a total of 49 protein pairs in pDONR223 plasmid were picked from the hORFeome v8.1 library. The bait and prey protein of each protein pair was cloned into the expression plasmids containing the complementation fragments of a fluorescent protein Venus using Gateway LR reactions. The success of the LR reactions with desired ORF was confirmed by PCR using the plasmid-specific primers. To perform PCA, HEK293T cells were cultured in Dulbecco's Modified Eagle Medium (DMEM) supplemented with 10% fetal bovine serum (FBS) (ATCC) in black 96-well flat-bottom plates (Costar) with 5% $CO_2$ at 37° C. At 60-70% confluency, the cells were co-transfected with the plasmids containing the bait and prey ORF (100 ng for each) pre-mixed with polyethylenimine (PEI) (Polysciences Inc.) and OptiMEM (Gibco). A total of 49 bait and prey ORF pairs along with previously published 45 positive reference pairs and 45 negative reference pairs were examined and distributed across different plates. After 68 hours, the fluorescence of the transfected cells was measured using Infinite M1000 microplate reader (Tecan) (excitation=514±5 nm/emission=527±5 nm). The p-values were calculated using a paired one-tailed t-test.

Data Processing

The raw data files were converted and the spectra were exported as .mgf (MS1 spectra as .dta) files using Proteome Discoverer 2.1 software (PD 2.1). SEQUEST searches were performed using PD 2.1 with the following settings: precursor mass tolerance: 20 ppm (10 ppm for MS2 rescue module); MS3 fragment ion mass tolerance: 0.6 Da (0.05 Da for MS2 rescue module); fixed modification: Cys carbamidomethylation; variable modifications: Met oxidation, Long arm of DSSO, Short arm of DSSO; max. equal modification per peptide: 3; max. missed cleavages: 3, minimum peptide length: 5. Concatenated target-decoy databases are used for various PSM searches performed during the evaluations. Target sequences were downloaded from uniport database (with filter "reviewed") and a corresponding decoy database was generated by randomizing the sequences using an in-house python script. The target sequences included: (i) *E. coli:* 5268 sequences; downloaded on 28 Oct. 2017, (ii) *S. cerevisiae:* 7904 sequences; downloaded on 28 Sep. 2017, and (iii) *Homo Sapiens:* 42202 sequences; downloaded on 23 Jun. 2017.

What is claimed is:

1. An apparatus comprising:
   a processing platform comprising one or more processing devices each including at least one processor coupled to a memory;
   the processing platform being configured to implement a crosslink identification and validation algorithm for processing multiple levels of mass spectrometry data in order to identify and validate protein-protein interactions within the mass spectrometry data, wherein the multiple levels of mass spectrometry data comprise MS1, MS2 and MS3 levels of mass spectrometry data comprising respective MS1, MS2 and MS3 spectra;
   wherein in conjunction with execution of the crosslink identification and validation algorithm, the processing platform is further configured:
   to obtain mass spectrometry spectra for each of the multiple levels;
   to apply a header matching filter to identify at least one potential crosslink relating one or more first level spectra and one or more second level spectra utilizing a plurality of third level spectra, the header matching filter being configured to identify a plurality of MS3 spectra having a common header and to identify the potential crosslink based at least in part on the identified MS3 spectra having the common header;
   to apply one or more mass validation filters to identify whether or not the potential crosslink is a valid crosslink;
   responsive to the potential crosslink being identified as a valid crosslink by each of the one or more mass validation filters, to generate a confidence score for the valid crosslink; and
   to take one or more automated actions based at least in part on the valid crosslink and its confidence score.

2. The apparatus of claim 1 wherein the processing platform is configured to iterate operations of the crosslink identification and validation algorithm in order to identify and validate a plurality of crosslinks based on respective different sets of mass spectrometry data.

3. The apparatus of claim 1 wherein the header matching filter determines the common header based at least in part on precursor mass and charge state entries of headers of the MS1, MS2 and MS3 spectra.

4. The apparatus of claim 1 wherein the header matching filter is configured to relate the identified MS3 spectra to their corresponding MS1 and MS2 spectra.

5. The apparatus of claim 1 wherein the one or more mass validation filters comprise at least one of:
a mass matching validation filter; and
a mass validation filter based at least in part on peptide spectrum match (PSM) data.

6. The apparatus of claim 1 wherein the potential crosslink is identified as one of an interprotein crosslink and an intraprotein crosslink.

7. The apparatus of claim 1 wherein the processing platform is further configured to receive at least portions of the mass spectrometry data over a network from a mass spectrometry system.

8. The apparatus of claim 1 wherein the one or more automated actions comprise at least one of:
reporting the valid crosslink and its confidence score over a network to at least one user terminal;
generating at least a portion of at least one output display comprising at least one of the valid crosslink and its confidence score for presentation on the user terminal;
generating an alert based at least in part on the valid crosslink and its confidence score for delivery to the user terminal over the network; and
storing the valid crosslink and its confidence score in at least one crosslink database accessible to the processing platform.

9. An apparatus comprising:
a processing platform comprising one or more processing devices each including at least one processor coupled to a memory;
the processing platform being configured to implement a crosslink identification and validation algorithm for processing multiple levels of mass spectrometry data in order to identify and validate protein-protein interactions within the mass spectrometry data, wherein the multiple levels of mass spectrometry data comprise MS1, MS2 and MS3 levels of mass spectrometry data comprising respective MS1, MS2 and MS3 spectra;
wherein in conjunction with execution of the crosslink identification and validation algorithm, the processing platform is further configured:
to obtain mass spectrometry spectra for each of the multiple levels;
to apply a header matching filter to identify at least one potential crosslink relating one or more first level spectra and one or more second level spectra utilizing a plurality of third level spectra;
to apply one or more mass validation filters to identify whether or not the potential crosslink is a valid crosslink;
responsive to the potential crosslink being identified as a valid crosslink by each of the one or more mass validation filters, to generate a confidence score for the valid crosslink; and
to take one or more automated actions based at least in part on the valid crosslink and its confidence score;
wherein the one or more mass validation filters comprise at least a mass matching validation filter; and
wherein the mass matching validation filter is configured:
to identify an MS2 precursor mass for the potential crosslink;
to identify a combination of MS3 precursor masses;
to confirm that the combination of MS3 precursor masses is consistent with the MS2 precursor mass; and
to confirm presence of each of the MS3 precursor masses of the combination of MS3 precursor masses in the corresponding MS2 spectra.

10. An apparatus comprising:
a processing platform comprising one or more processing devices each including at least one processor coupled to a memory;
the processing platform being configured to implement a crosslink identification and validation algorithm for processing multiple levels of mass spectrometry data in order to identify and validate protein-protein interactions within the mass spectrometry data, wherein the multiple levels of mass spectrometry data comprise MS1, MS2 and MS3 levels of mass spectrometry data comprising respective MS1, MS2 and MS3 spectra;
wherein in conjunction with execution of the crosslink identification and validation algorithm, the processing platform is further configured:
to obtain mass spectrometry spectra for each of the multiple levels;
to apply a header matching filter to identify at least one potential crosslink relating one or more first level spectra and one or more second level spectra utilizing a plurality of third level spectra;
to apply one or more mass validation filters to identify whether or not the potential crosslink is a valid crosslink;
responsive to the potential crosslink being identified as a valid crosslink by each of the one or more mass validation filters, to generate a confidence score for the valid crosslink; and
to take one or more automated actions based at least in part on the valid crosslink and its confidence score;
wherein the one or more mass validation filters comprise at least a mass validation filter based at least in part on peptide spectrum match (PSM) data; and
wherein the mass validation filter based at least in part on PSM data is configured:
to parse the PSM data to identify a set of candidate peptides for the potential crosslink;
to confirm presence of at least a threshold minimum number of PSMs per candidate peptide;
to combine masses of the candidate peptides and an associated linker; and
to confirm that the combination of masses of the candidate peptides and the associated linker is consistent with an MS2 precursor mass of the potential crosslink.

11. The apparatus of claim 10 wherein the threshold minimum number of PSMs per candidate peptide is one PSM per candidate peptide.

12. The apparatus of claim 10 wherein the associated linker comprises a DSSO linker.

13. The apparatus of claim 10 wherein the mass validation filter based at least in part on PSM data is configured:
to determine if there are sequences of at least two PSMs per candidate peptide;
responsive to there being sequences of at least two PSMs per candidate peptide, to determine if there is a match between the sequences; and
responsive to presence of a match between the sequences, combining the masses of the candidate peptides and the associated linker, and confirming that the combination of masses is consistent with the MS2 precursor mass; and responsive to absence of a match between the sequences, rejecting the potential crosslink.

14. The apparatus of claim 10 wherein the confidence score for the valid crosslink is generated based at least in part on one or more of:
   at least one resealed q-value;
   one or more weights for respective PSM confidence levels; and
   one or more weights for crosslink recurrency.

15. An apparatus comprising:
   a processing platform comprising one or more processing devices each including at least one processor coupled to a memory;
   the processing platform being configured to implement a crosslink identification and validation algorithm for processing multiple levels of mass spectrometry data in order to identify and validate protein-protein interactions within the mass spectrometry data, wherein the multiple levels of mass spectrometry data comprise MS1, MS2 and MS3 levels of mass spectrometry data comprising respective MS1, MS2 and MS3 spectra;
   wherein in conjunction with execution of the crosslink identification and validation algorithm, the processing platform is further configured:
   to obtain mass spectrometry spectra for each of the multiple levels;
   to apply a header matching filter to identify at least one potential crosslink relating one or more first level spectra and one or more second level spectra utilizing a plurality of third level spectra;
   to apply one or more mass validation filters to identify whether or not the potential crosslink is a valid crosslink;
   responsive to the potential crosslink being identified as a valid crosslink by each of the one or more mass validation filters, to generate a confidence score for the valid crosslink; and
   to take one or more automated actions based at least in part on the valid crosslink and its confidence score;
   wherein the one or more mass validation filters comprise at least one of:
   a mass matching validation filter; and
   a mass validation filter based at least in part on peptide spectrum match (PSM) data; and
   wherein responsive to at least one of:
   (i) a failure of the mass matching validation filter to confirm validity of an MS2 precursor mass for the potential crosslink; and
   (ii) a failure of the mass validation filter based at least in part on PSM data to obtain reliable PSM data for at least one candidate peptide;
   an MS2 rescue module is triggered for the potential crosslink.

16. The apparatus of claim 15 wherein the MS2 rescue module initially determines if there is at least one peptide reliably identified from corresponding MS3 spectra and terminates if there is no such reliably identified peptide.

17. The apparatus of claim 16 wherein responsive to there being at least one reliably identified peptide, the MS2 rescue module is further configured:
   to derive MS3 precursor masses for a non-reliably identified peptide using an MS2 precursor mass for the potential crosslink and MS3 precursor masses for the reliably identified peptide;
   to determine if the corresponding MS2 spectra contain the derived MS3 precursor masses; and
   responsive to the corresponding MS2 spectra containing the derived MS3 precursor masses, to perform a PSM search utilizing the MS2 spectra and the derived MS3 precursor masses.

18. The apparatus of claim 17 wherein performing the PSM search comprises:
   performing a first PSM search on a first MS2 spectrum using a first one of the derived precursor masses; and
   performing a second PSM search on a second MS2 spectrum using a second one of the derived precursor masses.

19. The apparatus of claim 17 wherein responsive to the PSM search yielding at least one PSM, performing further evaluation of the candidate peptide for the potential crosslink using said at least one PSM.

20. The apparatus of claim 15 wherein the MS2 rescue module is further triggered for the potential crosslink responsive to detection of corresponding MS3 spectra representing different charge states of a single candidate peptide.

21. An apparatus comprising:
   a processing platform comprising one or more processing devices each including at least one processor coupled to a memory;
   the processing platform being configured to implement a crosslink identification and validation algorithm for processing multiple levels of mass spectrometry data in order to identify and validate protein-protein interactions within the mass spectrometry data;
   wherein in conjunction with execution of the crosslink identification and validation algorithm, the processing platform is further configured:
   to obtain mass spectrometry spectra for each of the multiple levels;
   to apply a header matching filter to identify at least one potential crosslink relating one or more first level spectra and one or more second level spectra utilizing a plurality of third level spectra;
   to apply one or more mass validation filters to identify whether or not the potential crosslink is a valid crosslink;
   responsive to the potential crosslink being identified as a valid crosslink by each of the one or more mass validation filters, to generate a confidence score for the valid crosslink; and
   to take one or more automated actions based at least in part on the valid crosslink and its confidence score;
   wherein the processing platform is further configured to implement a machine learning system, the machine learning system being configured to separate a plurality of crosslinks into respective training and testing sets and to process at least the training sets against a database of known protein-protein interactions.

22. The apparatus of claim 21 wherein the machine learning system further comprises a neural network configured to assign probability scores to respective ones of the crosslinks of at least the training set.

23. A method comprising:
   obtaining mass spectrometry data comprising mass spectrometry spectra for each of multiple levels of the mass spectrometry data, wherein the multiple levels of mass spectrometry data comprise MS1, MS2 and MS3 levels of mass spectrometry data comprising respective MS1, MS2 and MS3 spectra;
   applying a header matching filter to identify at least one potential crosslink relating one or more first level spectra and one or more second level spectra utilizing a plurality of third level spectra, the header matching filter being configured to identify a plurality of MS3 spectra having a common header and to identify the potential crosslink based at least in part on the identified MS3 spectra having the common header;

applying one or more mass validation filters to identify whether or not the potential crosslink is a valid crosslink;

responsive to the potential crosslink being identified as a valid crosslink by each of the one or more mass validation filters, generating a confidence score for the valid crosslink; and taking one or more automated actions based at least in part on the valid crosslink and its confidence score;

wherein the method is performed by a processing platform comprising at least one processing device comprising a processor coupled to a memory.

24. The method of claim 23 wherein the header matching filter is configured to identify the potential crosslink by relating the plurality of MS3 spectra to corresponding MS1 and MS2 spectra via the common header.

25. The method of claim 23 wherein the one or more mass validation filters comprise at least one of:
a mass matching validation filter; and
a mass validation filter based at least in part on peptide spectrum match (PSM) data.

26. The method of claim 23 further comprising implementing a machine learning system, the machine learning system being configured to separate a plurality of crosslinks into respective training and testing sets and to process at least the training sets against a database of known protein-protein interactions.

27. A computer program product comprising a non-transitory processor-readable storage medium having stored therein program code of one or more software programs, wherein the program code when executed by at least one processing device of a processing platform causes the processing platform:

to obtain mass spectrometry data comprising mass spectrometry spectra for each of multiple levels of the mass spectrometry data, wherein the multiple levels of mass spectrometry data comprise MS1, MS2 and MS3 levels of mass spectrometry data comprising respective MS1, MS2 and MS3 spectra;

to apply a header matching filter to identify at least one potential crosslink relating one or more first level spectra and one or more second level spectra utilizing a plurality of third level spectra, the header matching filter being configured to identify a plurality of MS3 spectra having a common header and to identify the potential crosslink based at least in part on the identified MS3 spectra having the common header;

to apply one or more mass validation filters to identify whether or not the potential crosslink is a valid crosslink;

responsive to the potential crosslink being identified as a valid crosslink by each of the one or more mass validation filters, to generate a confidence score for the valid crosslink; and to take one or more automated actions based at least in part on the valid crosslink and its confidence score.

28. The computer program product of claim 27 wherein the header matching filter is configured to identify the potential crosslink by relating the plurality of MS3 spectra to corresponding MS1 and MS2 spectra via the common header.

29. The computer program product of claim 27 wherein the one or more mass validation filters comprise at least one of:
a mass matching validation filter; and
a mass validation filter based at least in part on peptide spectrum match (PSM) data.

30. The computer program product of claim 27 wherein the program code when executed by the at least one processing device of the processing platform further causes the processing platform to implement a machine learning system, the machine learning system being configured to separate a plurality of crosslinks into respective training and testing sets and to process at least the training sets against a database of known protein-protein interactions.

* * * * *